US007960417B2

(12) United States Patent
Govek et al.

(10) Patent No.: US 7,960,417 B2
(45) Date of Patent: Jun. 14, 2011

(54) BENZAZOLE POTENTIATORS OF METABOTROPIC GLUTAMATE RECEPTORS

(75) Inventors: Steven P. Govek, San Diego, CA (US); Jean-Michel Vernier, Laguna Niguel, CA (US); Theodore Kamenecka, Palm Beach Gardens, NJ (US); John H. Hutchinson, La Jolla, CA (US); Richard Pracitto, North Wales, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 902 days.

(21) Appl. No.: 11/884,391

(22) PCT Filed: Feb. 17, 2006

(86) PCT No.: PCT/US2006/005711
§ 371 (c)(1),
(2), (4) Date: Aug. 14, 2007

(87) PCT Pub. No.: WO2006/091496
PCT Pub. Date: Aug. 31, 2006

(65) Prior Publication Data
US 2008/0176904 A1 Jul. 24, 2008

Related U.S. Application Data

(60) Provisional application No. 60/656,113, filed on Feb. 24, 2005, provisional application No. 60/666,361, filed on Mar. 30, 2005.

(51) Int. Cl.
*A61K 31/41* (2006.01)
*A61K 31/4192* (2006.01)
*C07D 403/12* (2006.01)
*C07D 249/20* (2006.01)
*C07D 249/18* (2006.01)

(52) U.S. Cl. ......... 514/359; 514/381; 548/252; 548/260
(58) Field of Classification Search .................. 548/252, 548/260; 514/381, 359
See application file for complete search history.

(56) References Cited

U.S. PATENT DOCUMENTS

| 4,096,267 | A | 6/1978 | Cragoe et al. |
| 4,177,285 | A | 12/1979 | Cragoe et al. |
| 4,182,764 | A | 1/1980 | Cragoe et al. |
| 4,874,775 | A | 10/1989 | Krumkalns et al. |
| 4,983,628 | A | 1/1991 | Frenette et al. |
| 6,380,218 | B1 | 4/2002 | Marfat et al. |
| 6,482,834 | B2 | 11/2002 | Spada et al. |
| 2002/0006948 | A1 | 1/2002 | Halfbrodt et al. |

FOREIGN PATENT DOCUMENTS

| EP | 1403255 A1 | 3/2004 |
| WO | WO 01/56990 | 8/2001 |
| WO | 2004018386 A2 | 3/2004 |
| WO | WO 2004/018386 | 3/2004 |
| WO | 2004108686 A2 | 12/2004 |
| WO | WO 2006/014918 | 2/2006 |
| WO | WO 2006/015158 | 2/2006 |
| WO | WO 2006/047237 | 5/2006 |
| WO | WO 2006/049968 | 5/2006 |

OTHER PUBLICATIONS

O. W. Woltersdorf et al., "(Acylaryloxy) Acetic Acid Diuretics. 1. (2-Alkyl-and 2,2-Dialkyl-1-Oxo-5-Indanyloxy) Acetic Acids", J. of Medicinal Chemistry, 1977, vol. 20. No. 11, pp. 1400-1408.

S. J. deSolms et al., "(Acylaryloxy) Acetic Acid Diuretics. 2. (2-Alkyl-2-Aryl-1-oxo-5 Indanyloxy) Acetic Acids", J. of Medicinal Chemistry, 1978, vol. 21, No. 5, pp. 437-443.

M. P. Johnson et al., "Discovery of Allosteric Potentiators for the Metabotropic Glutamate 2 Receptor: Synthesis and Subtype Selectivity of N-(4-(2-Methoxyphenoxy)phenyl)-N(2,2,2-Trifluoroethylsulfonyl) Pyrid-3-Ylmethyl-Amine", J. Med. Chem., 2003, vol. 46, pp. 3189-3192.

A. B. Pinkerton et al., "Allosteric Potentiators of the Metabotropic Glutamate Receptor 2 (mGlu2). Part 1: Identification and Synteheis of Phenyl-Tetrazolyl Acetophenones", Bioorganic & Medicinal Chemistry Letters, 2004, vol. 14, pp. 5329-5332.

A. B. Pinkerton et al., "Allosteric Potentiators of the Metabotropic Glutamate Receptor 2 (mGlu2). Part 2: 4-Thiopyridyl Acetophenones as Non-Terazole Containing mG1u2 Receptor Potentiators", Bioorganic & Medicinal Chemistry Letters, 2004, vol. 14, pp. 5867-5872.

A. B. Pinkerton et al., A. B. Pinkerton et al., "Allosteric Potentiators of the Metabotropic Glutamate Receptor 2 (mGlu2). Part 3: 4-Thiopyridyl Acetophenones as Non-Terazole Containing mGlu2 Receptor Potentiators", Bioorganic & Medicinal Chemistry Letters, 2005, vol. 15, pp. 1565-1571.

Susumu Igarashi, et al., 'A novel class of inhibitors for human steroid 5-alpha-reductase: synthesis and biological evaluation of indole derivatives', Chemical and Pharmaceutical Bulletin, vol. 48, No. 3, 2000, pp. 382-388.

Susumu Igarashi, et al., 'A novel class of inhibitors for human and rat steroid 5-alpha-reductases: synthesis and biological evaluation of indole and aniline derivatives', Chemical and Pharmaceutical Bulletin, vol. 48, No. 11, 2000, pp. 1689-1697.

(Continued)

*Primary Examiner* — Patricia L Morris
(74) *Attorney, Agent, or Firm* — Gerard Devlin; Raynard Yuro

(57) ABSTRACT

The present invention is directed to benzazole compounds which are potentiators of metabotropic glutamate receptors, including the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

15 Claims, No Drawings

OTHER PUBLICATIONS

Alan D. Adams, et al., 'Amphipathic 3-phenyl-7-propylbenzisoxazoles; human PPAR gamma, delta and alpha agonists', Bioorganic & Medicinal Chemistry Letters, vol. 13, No. 5, 2003, pp. 931-935.

Steven P. Govek, et al., 'Benzazoles as allosteric potentiators of metabotropic glutamate receptor 2 (mGluR2): efficacy in an animal model for schizophrenia', Bioorganic & Medicinal Chemistry Letters, vol. 15, No. 18, 2005, pp. 4068-4072.

Youhua Yang and Arnold R. Martin, 'Synthesis of 5-arylated indoles via palladium-catalyzed cross-coupling reaction of 5-indolylboronic acid with aryl and heteroaryl halides', Heterocycles, vol. 34, No. 7, 1992, pp. 1395-1398.

Mark T. Bilodeau, et al., 'Design and synthesis of 1,5-diarylbenzimidazoles as inhibitors of the VEGF-receptor KDR', Bioorganic & Medicinal Chemistry Letters, vol. 13, 2003, pp. 2485-2488.

Eckhard Baston & Rolf W. Hartmann, 'N-substituted 4-(5-indolyl)benzoic acids synthesis and evaluation of steriod 5 alpha-reductase type I and II inhibitory activity', Bioorganic & Medicinal Chemistry Letters, vol. 9, No. 11, 1999, pp. 1601-1606.

C. W. Schellhammer, et al., 'Uber alkylierungen von benzotriazol-derivaten', Tetrahedron, vol. 26, No. 2, 1970, pp. 497-510.

Wayne K. Anderson, et al., 'Design, synthesis, and study of 9-substituted ellipticine and 2-methylellipticinium analogues as potential CNS-selective antitumor agents', Journal of Medicinal Chemistry, vol. 37, No. 13, 1994, pp. 1955-1963.

Supplementary Partial European Search Report for PCT/US2006/005711, mailed Apr. 6, 2010.

BENZAZOLE POTENTIATORS OF METABOTROPIC GLUTAMATE RECEPTORS

CROSS REFERENCE TO RELATED APPLICATIONS

This application is a U.S. National Phase application under 35 U.S.C. §371 of PCT Application No. PCT/US2006/005711, filed Feb. 17, 2006, which claims priority under 35 U.S.C. §119 from U.S. Application No. 60/656,113, filed Feb. 24, 2005 and U.S. Application No. 60/666,361 filed Mar. 30, 2005.

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGluR) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The present invention relates to potentiators of mGlu receptors, in particular mGluR2 receptors. The mGluR receptors belong to the Type III G-protein coupled receptor (GPCR) superfamily. This superfamily of GPCR'sf including the calcium-sensing receptors, GABAB receptors and pheromone receptors, which are unique in that they are activated by binding of effectors to the amino-terminus portion of the receptor protein. The mGlu receptors are thought to mediate glutamate's demonstrated ability to modulate intracellular signal transduction pathways. Ozawa, Kamiya and Tsuzuski, Prog. Neurobio., 54, 581 (1998). They have been demonstrated to be localized both pre- and post-synaptically where they can regulate neurotransmitter release, either glutamate or other neurotransmitters, or modify the post-synaptic response of neurotransmitters, respectively.

At present, there are eight distinct mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGluR receptors, which include the mGlu1R and mGlu5R, are known to activate phospholipase C (PLC) via Gaq-proteins thereby resulting in the increased hydrolysis of phosphoinositides and intracellular calcium mobilization. There are several compounds that are reported to activate the Group I mGlu receptors including DHPG, (R/S)-3,5-dihydroxyphenylglycine. Schoepp, Goldworthy, Johnson, Salhoff and Baker, J. Neurochem., 63, 769 (1994); Ito, et al., keurorep., 3, 1013 (1992). The Group II mGlu receptors consist of the two distinct receptors, mGluR2 and mGluR3 receptors. Both have been found to be negatively coupled to adenylate cyclase via activation of Gai-protein. These receptors can be activated by a selective compound such as 1S,2S,SR,6S-2 aminobicyclo [3.1.0]hexane-2,6-dicarboxylate. Monn, et al., J. Med. Chem., 40, 528 (1997); Schoepp, et al., Neuropharmacol., 36, 1 (1997). Similarly, the Group III mGlu receptors, including mGluR4, mGluR6, mGluR7 and mGluR8, are negatively coupled to adenylate cyclase via Gai and are potently activated by L-AP4 (L-(+)-2-amino-4-phosphonobutyric acid). Schoepp, Neurochem. Int., 24, 439 (1994).

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction makes the abatement of these neurological processes an important therapeutic goal.

SUMMARY OF THE INVENTION

The present invention is directed to compounds which are potentiators of metabotropic glutamate receptors, including the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

DETAILED DESCRIPTION OF THE INVENTION

The present invention is directed to compounds of the formula I:

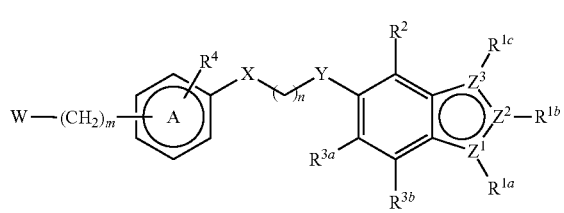

wherein:
A is phenyl or pyridyl;
W is selected from the group consisting of:
   (1) -tetrazolyl,
   (2) —$CO_2H$,
   (3) —$NHSO_2C_{1-6}$alkyl,
   (4) —$NHSO_2$-phenyl, wherein the phenyl is unsubstituted or substituted with $C_{1-6}$alkyl, and
   (5) —CONHCO—$C_{1-6}$alkyl,
   (6) hydrogen;

X is selected from the group consisting of:
  (1) —O—,
  (2) —O—$C_{1-6}$alkyl-,
  (3) —O—$C_{2-6}$alkenyl-,
  (4) a bond,
  (5) —O—$C_{3-7}$cycloalkyl -
  (6) -pyrrolidine-,
  (7) -piperidine-,
  (8) —S—,
  (9) —O-phenyl-, wherein the phenyl is unsubstituted or substituted with $C_{1-6}$alkyl, or halogen,
  (10) —S-phenyl-, wherein the phenyl is unsubstituted or substituted with $C_{1-6}$alkyl, or halogen, and
  (11) -phenyl-, wherein the phenyl is unsubstituted or substituted with $C_{1-6}$alkyl, or halogen;
Y is selected from the group consisting of:
  (1) —O—,
  (2) —NH(CO)—, and
  (3) a bond;
$Z^1$, $Z^2$ and $Z^3$ are selected from C, N and O such that together with the fused phenyl ring they form an indolyl, indolinyl, indazolyl, benzimidazolyl, benzoxazolyl, benzisoxazolyl, or benzotriazolyl ring;
$R^{1a}$, $R^{1b}$ and $R^{1c}$ may be absent if the valency at $Z^1$, $Z^2$ or $Z^3$ does not permit such substitution and are independently selected from the group consisting of:
  (1) hydrogen,
  (2) $C_{1-6}$alkyl, which is unsubstituted or substituted with a substituent selected from:
    (a) halogen,
    (b) hydroxyl,
    (c) phenyl, wherein the phenyl is unsubstituted or substituted with 1-5 substituents independently selected from halogen, cyano, $CF_3$, hydroxyl, $C_{1-6}$alkyl, pyridyl, pyrimidinyl, pyrrolidinyl, pyrrolyl, and $OC_{1-6}$alkyl,
    (d) $C_{3-7}$cycloalkyl, which is unsubstituted or substituted with halogen, hydroxyl or phenyl,
    (e) pyridyl, which is unsubstituted or substituted with halogen, $C_{1-6}$alkyl or phenyl,
    (f) naphthyl, which is unsubstituted or substituted with halogen, $C_{1-6}$alkyl or phenyl,
    (g) tetrahydropyranyl, which is unsubstituted or substituted with halogen, $C_{1-6}$alkyl or phenyl, and
    (h) isoxazolyl, which is unsubstituted or substituted with halogen, $C_{1-6}$alkyl or phenyl,
    (i) —CO—$C_{1-6}$alkyl, and
    (j) —COO—$C_{1-6}$alkyl,
  (3) $C_{3-7}$cycloalkyl, which is unsubstituted or substituted with halogen, $C_{1-6}$alkyl, hydroxyl or phenyl,
  (4) phenyl, wherein the phenyl is unsubstituted or substituted with 1-5 substituents independently selected from halogen, hydroxyl, cyano, $CF_3$, $C_{1-6}$alkyl, and $OC_{1-6}$alkyl, wherein the $C_{1-6}$alkyl and $OC_{1-6}$alkyl are linear or branched and optionally substituted with 1-5 halogen,
  (5) —CO—$C_{1-6}$alkyl, and
  (6) —COO—$C_{1-6}$alkyl;
$R^2$ is selected from the group consisting of:
  (1) hydrogen,
  (2) halogen,
  (3) hydroxyl,
  (4) $OC_{1-6}$alkyl,
  (5) $C_{2-6}$alkenyl, and
  (6) $C_{1-6}$alkyl, which is unsubstituted or substituted with halogen, hydroxyl or phenyl;

$R^{3a}$ and $R^{3b}$ are selected from the group consisting of:
  (1) hydrogen,
  (2) halogen,
  (3) $C_{1-6}$alkyl, which is unsubstituted or substituted with halogen, hydroxyl or phenyl, and
  (4) $OC_{1-6}$alkyl;
$R^4$ may include multiple substituents and is independently selected from the group consisting of:
  (1) hydrogen,
  (2) halogen,
  (3) $C_{1-6}$alkyl, and
  (4) —O—$C_{1-6}$alkyl;
m is an integer selected from 0, 1, 2 and 3;
n is an integer selected from 0, 1, 2, 3, 4, 5 and 6;
and pharmaceutically acceptable salts thereof and individual diastereomers thereof.

An embodiment of the present invention includes compounds of the formula Ia:

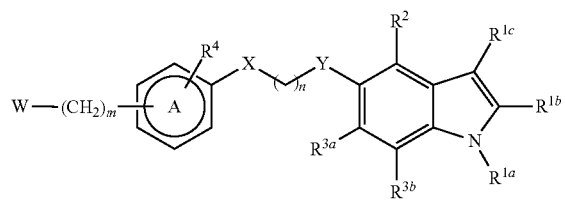

Ia wherein $R^{1a}$, $R^{1b}$, $R^{1c}$, $R^2$, $R^{3a}$, $R^{3b}$, $R^4$, A, W, X, Y, n and m are defined herein;

or a pharmaceutically acceptable salt thereof or an individual enantiomer or diastereomer thereof.

An embodiment of the present invention includes compounds of the formula Ib:

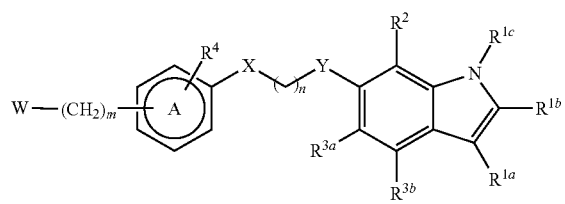

Ib wherein $R^{1a}$, $R^{1b}$, $R^{1c}$, $R^2$, $R^{3a}$, $R^{3b}$, $R^4$, A, X, Y, n and m are defined herein;

or a pharmaceutically acceptable salt thereof or an individual enantiomer or diastereomer thereof.

An embodiment of the present invention includes compounds of the formula Ic:

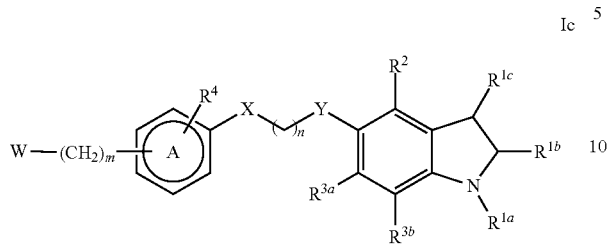

Ic wherein $R^{1a}$, $R^{1b}$, $R^{1c}$, $R^2$, $R^{3a}$, $R^{3b}$, $R^4$, A, X, Y, n and m are defined herein;
or a pharmaceutically acceptable salt thereof or an individual enantiomer or diastereomer thereof.

An embodiment of the present invention includes compounds of the formula Id:

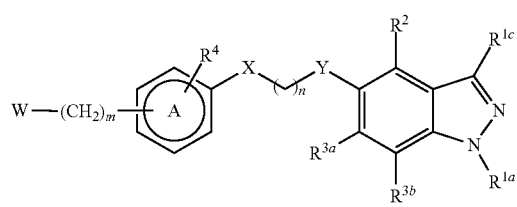

Id wherein $R^{1a}$, $R^{1c}$, $R^2$, $R^{3a}$, $R^{3b}$, $R^4$, A, X, Y, n and m are defined herein;
or a pharmaceutically acceptable salt thereof or an individual enantiomer or diastereomer thereof.

An embodiment of the present invention includes compounds of the formula Ie:

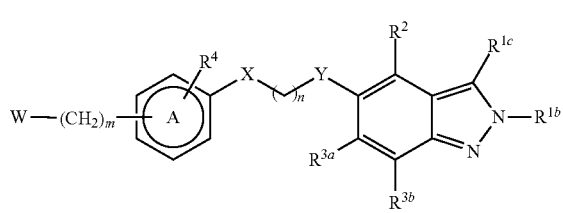

Ie wherein $R^{1b}$, $R^{1c}$, $R^2$, $R^{3a}$, $R^{3b}$, $R^4$, A, X, Y, n and m are defined herein;
or a pharmaceutically acceptable salt thereof or an individual enantiomer or diastereomer thereof.

An embodiment of the present invention includes compounds of the formula If:

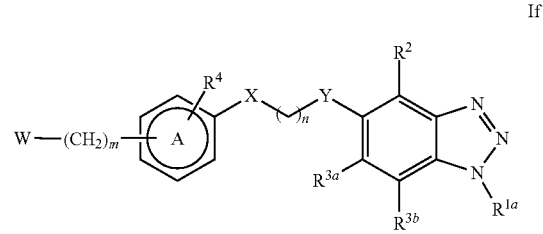

If wherein $R^{1a}$, $R^2$, $R^{3a}$, $R^{3b}$, $R^4$, A, X, Y, n and m are defined herein;
or a pharmaceutically acceptable salt thereof or an individual enantiomer or diastereomer thereof.

An embodiment of the present invention includes compounds of the formula Ig:

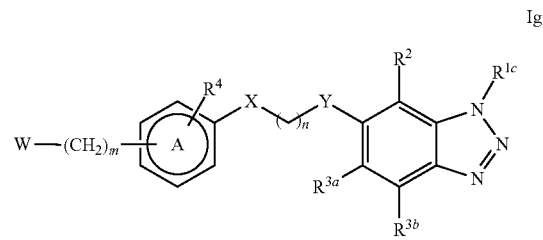

Ig wherein $R^{1c}$, $R^2$, $R^{3a}$, $R^{3b}$, $R^4$, A, X, Y, n and m are defined herein;
or a pharmaceutically acceptable salt thereof or an individual enantiomer or diastereomer thereof.

An embodiment of the present invention includes compounds of the formula Ih:

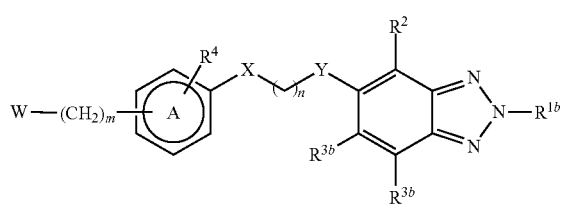

Ih wherein $R^{1b}$, $R^2$, $R^{3a}$, $R^{3b}$, $R^4$, A, X, Y, n and m are defined herein;
or a pharmaceutically acceptable salt thereof or an individual enantiomer or diastereomer thereof.

An embodiment of the present invention includes compounds of the formula Ii:

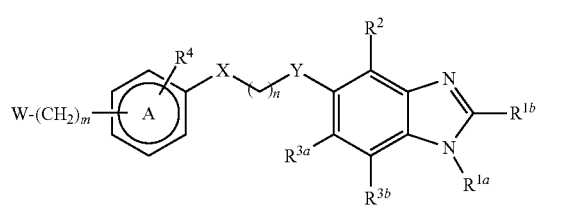

Ii wherein $R^{1a}$, $R^{1b}$, $R^2$, $R^{3a}$, $R^{3b}$, $R^4$, A, X, Y, n and m are defined herein;

or a pharmaceutically acceptable salt thereof or an individual enantiomer or diastereomer thereof.

An embodiment of the present invention includes compounds of the formula Ij:

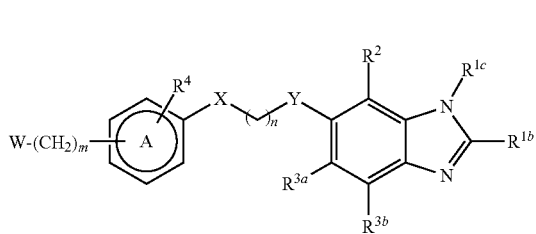

Ij wherein $R^{1b}$, $R^{1c}$, $R^2$, $R^{3a}$, $R^{3b}$, $R^4$, A, X, Y, n and m are defined herein;

or a pharmaceutically acceptable salt thereof or an individual enantiomer or diastereomer thereof.

An embodiment of the present invention includes compounds of the formula Ik:

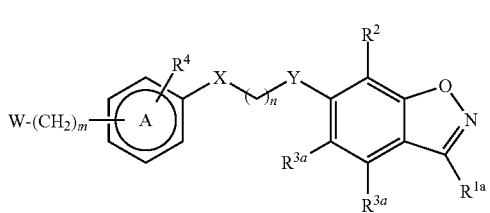

Ik wherein $R^{1a}$, $R^2$, $R^{3a}$, $R^{3b}$, $R^4$, A, X, Y, n and m are defined herein;

or a pharmaceutically acceptable salt thereof or an individual enantiomer or diastereomer thereof.

An embodiment of the present invention includes compounds wherein A is phenyl.

An embodiment of the present invention includes compounds wherein A is pyridyl.

An embodiment of the present invention includes compounds wherein W is tetrazolyl.

An embodiment of the present invention includes compounds wherein W is $CO_2H$.

An embodiment of the present invention includes compounds wherein W is hydrogen.

An embodiment of the present invention includes compounds wherein X is —O—.

An embodiment of the present invention includes compounds wherein X is —O—$C_{2-6}$alkenyl-.

An embodiment of the present invention includes compounds wherein X is —O-cyclopentane-.

An embodiment of the present invention includes compounds wherein X is a bond and Y is —O—.

An embodiment of the present invention includes compounds wherein X is a bond.

An embodiment of the present invention includes compounds wherein X is —O-phenyl-.

An embodiment of the present invention includes compounds wherein X is -phenyl-.

An embodiment of the present invention includes compounds wherein X is -piperidine-.

An embodiment of the present invention includes compounds wherein X is -pyrrolidine-.

An embodiment of the present invention includes compounds wherein Y is —O—.

An embodiment of the present invention includes compounds wherein $R^{1a}$, $R^{1b}$ and $R^{1c}$ are independently selected from hydrogen and $C_{1-6}$alkyl, which is unsubstituted or substituted with a substituent selected from,
(a) $C_{3-7}$cycloalkyl,
(b) pyridyl,
(c) naphthyl,
(d) tetrahydropyranyl, and
(e) isoxazolyl.

An embodiment of the present invention includes compounds wherein $R^{1a}$, $R^{1b}$ and $R^{1c}$ are independently selected from hydrogen, $CH_3$, $CH_2CH_2CH_3$, $CH_2CH(CH_3)_2$, $CH_2CH_2CH_2CH_3$, $CH_2C(CH_3)_3$, $CH_2$-cyclopropyl, $CH_2$-cyclohexyl and phenyl.

An embodiment of the present invention includes compounds wherein $R^{1a}$, $R^{1b}$ and $R^{1c}$ are independently selected from hydrogen, $CH_2CH(CH_3)_2$, $CH_2CH_2CH_2CH_3$, $CH_2C(CH_3)_3$ and $CH_2$-cyclohexyl.

An embodiment of the present invention includes compounds wherein $R^{1a}$ is $CH_2C(CH_3)_3$.

An embodiment of the present invention includes compounds wherein $R^{1a}$ is $CH_2$-cyclohexyl.

An embodiment of the present invention includes compounds wherein $R^2$ is propyl.

An embodiment of the present invention includes compounds wherein $R^2$ is allyl.

An embodiment of the present invention includes compounds wherein $R^2$ is hydrogen.

An embodiment of the present invention includes compounds wherein $R^2$ is bromo.

An embodiment of the present invention includes compounds wherein $R^2$ is methyl.

An embodiment of the present invention includes compounds wherein $R^{3a}$ and $R^{3b}$ are hydrogen.

An embodiment of the present invention includes compounds wherein $R^4$ is hydrogen.

An embodiment of the present invention includes compounds wherein m is 0.

An embodiment of the present invention includes compounds wherein m is 1.

An embodiment of the present invention includes compounds wherein n is 1.

An embodiment of the present invention includes compounds wherein n is 4.

Specific embodiments of the present invention include a compound which is selected from the group consisting of:

1-(2,2-dimethylpropyl)-4-propyl-5-{4-[4-(1H-tetrazol-5-yl) phenoxy]butoxy}-1H-indole;

2,2-dimethyl-1-(7-propyl-6-{4-[4-(1H-tetrazol-5-yl)phenoxy]butoxy}-1H-indol-3-yl)propan-1-one;

1-(2,2-dimethylpropyl)-4-propyl-5-{4-[4-(1H-tetrazol-5-yl) phenoxy]butoxy}-1H-indazole;

2-(2,2-dimethylpropyl)-4-propyl-5-{4-[4-(1H-tetrazol-5-yl) phenoxy]butoxy}-2H-indazole;

1-(2,2-dimethylpropyl)-4-propyl-5-[4-(pyridin-3-yloxy)butoxy]-1H-indole;

1-(2,2-dimethylpropyl)-4-propyl-5-{4-[4-(1H-tetrazol-5-yl) phenoxy]butoxy}-1H-1,2,3-benzotriazole;

1-(2,2-dimethylpropyl)-7-propyl-6-{4-[4-(1H-tetrazol-5-yl) phenoxy]butoxy}-1H-1,2,3-benzotriazole;

1-(2,2-dimethylpropyl)-4-propyl-5-{4-[4-(1H-tetrazol-5-yl) phenoxy]butoxy}-1H-benzimidazole;

1-(2,2-dimethylpropyl)-7-propyl-6-{4-[4-(1H-tetrazol-5-yl)phenoxy]butoxy}-1H-benzimidazole;
1-(2,2-dimethylpropyl)-4-propyl-5-{4-[4-(1H-tetrazol-5-yl)phenoxy]butoxy}indoline;
4-bromo-1-(2,2-dimethylpropyl)-5-{4-[4-(1H-tetrazol-5-yl)phenoxy]butoxy}-1H-indole;
1-(2,2-dimethylpropyl)-5-{4-[4-(1H-tetrazol-5-yl)phenoxy]butoxy}-1H-indole;
1-(2,2-dimethylpropyl)-4-propyl-5-{[4-(1H-tetrazol-5-yl)benzyl]oxy}-1H-indole;
1-(2,2-dimethylpropyl)-4-propyl-5-{[3-(1H-tetrazol-5-yl)benzyl]oxy}-1H-indole;
1-(2,2-dimethylpropyl)-4-methyl-5-{4-[4-(1H-tetrazol-5-yl)phenoxy]butoxy}-1H-indole;
1-(2,2-dimethylpropyl)-2-methyl-4-propyl-5-{4-[4-(1H-tetrazol-5-yl)phenoxy]butoxy}-1H-indole;
ethyl 1-(2,2-dimethylpropyl)-4-propyl-5-{4-[4-(1H-tetrazol-5-yl)phenoxy]butoxy}-1H-indole-2-carboxylate;
1-(2,2-dimethylpropyl)-5-{4-[4-(1H-tetrazol-5-yl)phenoxy]butoxy}-1H-1,2,3-benzotriazole;
1-(2,2-dimethylpropyl)-6-{4-[4-(1H-tetrazol-5-yl)phenoxy]butoxy}-1H-1,2,3-benzotriazole;
1-(2,2-dimethylpropyl)-4-propyl-5-{[3'-(1H-tetrazol-5-yl)biphenyl-3-yl]methoxy}-1H-indole;
1-(2,2-dimethylpropyl)-4-propyl-5-{[4'-(2H-tetrazol-5-yl)biphenyl-3-yl]methoxy}-1H-indole;
4-bromo-1-(2,2-dimethylpropyl)-5-{4-[4-(1H-tetrazol-5-yl)phenoxy]butoxy}-1H-1,2,3-benzotriazole;
7-bromo-1-(2,2-dimethylpropyl)-6-{4-[4-(1H-tetrazol-5-yl)phenoxy]butoxy}-1H-1,2,3-benzotriazole;
1-(2,2-dimethylpropyl)-4-propyl-5-{2-[4-(1H-tetrazol-5-yl)phenoxy]ethoxy}-1H-indole;
1-(2,2-dimethylpropyl)-4-propyl-5-{3-[4-(1H-tetrazol-5-yl)phenoxy]propoxy}-1H-indole;
1-(2,2-dimethylpropyl)-4-propyl-5-({5-[4-(1H-tetrazol-5-yl)phenoxy]pentyl}oxy)-1H-indole;
3'-({[1-(2,2-dimethylpropyl)-4-propyl-1H-indol-5-yl]oxy}methyl)biphenyl-3-carboxylic acid;
3'-({[1-(2,2-dimethylpropyl)-4-propyl-1H-indol-5-yl]oxy}methyl)biphenyl-4-carboxylic acid;
1-(2,2-dimethylpropyl)-4-propyl-5-({1-[4-(2H-tetrazol-5-yl)phenyl]pyrrolidin-3-yl}methoxy)-1H-indole;
1-(2,2-dimethylpropyl)-4-propyl-5-({1-[4-(2H-tetrazol-5-yl)phenyl]piperidin-3-yl}methoxy)-1H-indole;
1-(2,2-dimethylpropyl)-4-propyl-5-({4-[4-(2H-tetrazol-5-yl)phenoxy]benzyl}oxy)-1H-indole;
4-allyl-1-(2,2-dimethylpropyl)-5-({3-[4-(H-tetrazol-5-yl)phenoxy]benzyl}oxy)-1H-indole;
1-(2,2-dimethylpropyl)-4-propyl-5-({3-[4-(1H-tetrazol-5-yl)phenoxy]benzyl}oxy)-1H-indole;
5-({2-chloro-5-[4-(1H-tetrazol-5-yl)phenoxy]benzyl}oxy)-1-(2,2-dimethylpropyl)-4-propyl-1H-indole;
1-(2,2-dimethylpropyl)-5-({2-ethyl-5-[4-(1H-tetrazol-5-yl)phenoxy]benzyl}oxy)-4-propyl-1H-indole;
1-(2,2-dimethylpropyl)-5-({2-fluoro-5-[4-(1H-tetrazol-5-yl)phenoxy]benzyl}oxy)-4-propyl-1H-indole;
4-3-({[1-(2,2-dimethylpropyl)-4-propyl-1H-indol-5-yl]oxy}methyl)pyrrolidin-1-yl]benzoic acid;
6-3-({[1-(2,2-dimethylpropyl)-4-propyl-1H-indol-5-yl]oxy}methyl)phenyl]pyridine-2-carboxylic acid;
5-[3-({[1-(2,2-dimethylpropyl)-4-propyl-1H-indol-5-yl]oxy}methyl)phenyl]nicotinic acid;
5-[3-({[1-(2,2-dimethylpropyl)-4-propyl-1H-indol-5-yl]oxy}methyl)phenyl]pyridine-2-carboxylic acid;
1-(2,2-dimethylpropyl)-4-propyl-5-({3-[5-(1H-tetrazol-5-yl)pyridin-3-yl]benzyl}oxy)-1H-indole;
1-(2,2-dimethylpropyl)-4-propyl-5-({3-[6-(2H-tetrazol-5-yl)pyridin-3-yl]benzyl}oxy)-1H-indole;
1-Cyclohexylmethyl-4-propyl-5-{4-[4-(2H-tetrazol-5-yl)-phenoxy]-butoxy}-1H-indole;
(4-Propyl-5-{4-[4-(2H-tetrazol-5-yl)-phenoxy]-butoxy}-indol-1-yl)-acetic acid tert-butyl ester;
4-Propyl-1-(tetrahydro-pyran-2-ylmethyl)-5-{4-[4-(2H-tetrazol-5-yl)-phenoxy]-butoxy}-1H-indole;
1-Naphthalen-2-ylmethyl-4-propyl-5-{4-[4-(2H-tetrazol-5-yl)-phenoxy]-butoxy}-1H-indole;
4-Propyl-1-(4-pyrrol-1-yl-benzyl)-5-{4-[4-(2H-tetrazol-5-yl)-phenoxy]-butoxy}-1H-indole;
(4-Propyl-5-{4-[4-(2H-tetrazol-5-yl)-phenoxy]-butoxy}-indol-1-yl)-acetic acid ethyl ester;
1-Cyclopropylmethyl-4-propyl-5-{4-[4-(2H-tetrazol-5-yl)-phenoxy]-butoxy}-1H-indole;
1,4-Dipropyl-5-{4-[4-(2H-tetrazol-5-yl)-phenoxy]-butoxy}-1H-indole;
1-(5-Methyl-isoxazol-3-ylmethyl)-4-propyl-5-{4-[4-(5H-[1,2,4]triazol-3-yl)-phenoxy]-butoxy}-1H-indol;
1-Isopropyl-4-propyl-5-{4-[4-(2H-tetrazol-5-yl)-phenoxy]-butoxy}-1H-indole;
1-(3-Methyl-butyl)-4-propyl-5-{4-[4-(2H-tetrazol-5-yl)-phenoxy]-butoxy}-1H-indole;
1-Isobutyl-4-propyl-5-{4-[4-(2H-tetrazol-5-yl)-phenoxy]-butoxy}-1H-indole;
1-Butyl-4-propyl-5-{4-[4-(2H-tetrazol-5-yl) -phenoxy]-butoxy}-1H-indole;
1-Pentyl-4-propyl-5-{4-[4-(2H-tetrazol-5-yl) -phenoxy]-butoxy}-1H-indole;
1-(2,2-Dimethyl-propyl)-4-propyl-5-{(E)-4-[4-(2H-tetrazol-5-yl)-phenoxy]-but-2-enyloxy}-1H-indole;
1-(2,2-Dimethyl-propyl)-4-propyl-5-{3-[4-(2H-tetrazol-5-yl)-phenoxy]-cyclopentyloxy}-1H-indole;
4-[1-(2,2-Dimethyl-propyl)-4-propyl-1H-indol-5-yloxymethyl]-benzoic acid;
4-{4-[1-(2,2-Dimethyl-propyl)-4-propyl-2H-benzotriazol-5-yloxy]-butoxy}-benzoic acid;
4-{4-[3-(2,2-Dimethyl-propyl)-4-propyl-3H-benzotriazol-5-yloxy]-butoxy}-benzoic acid;
4-{4-[2-(2,2-Dimethyl-propyl)-4-propyl-1H-benzotriazol-5-yloxy]-butoxy}-benzoic acid;
4-{4-[1-(2,2-Dimethyl-propyl)-4-propyl-1H-indol-5-yloxy]-butoxy}-benzoic acid;
3-ethyl-7-propyl-6-{4-[4-(1H-tetrazol-5-yl)phenoxy]butoxy}-1,2-benzisoxazole;
3-(2,2-dimethylpropyl)-7-propyl-6-{4-[4-(1H-tetrazol-5-yl)phenoxy]butoxy}-1,2-benzisoxazole;
3-cyclohexyl-7-propyl-6-{4-[4-(1H-tetrazol-5-yl)phenoxy]butoxy}-1,2-benzisoxazole;
1-benzyl-4-propyl-5-{4-[4-(1H-tetrazol-5-yl)phenoxy]butoxy}-1H-indole;
1-(2,2-dimethylpropanoyl)-4-propyl-5-{4-[4-(1H-tetrazol-5-yl)phenoxy]butoxy}-1H-indole;
1-(4-methylbenzyl-4-propyl-5-{4-[4-(1H-tetrazol-5-yl)phenoxy]butoxy}-1H-indole;
1-(3-methylbenzyl-4-propyl-5-{4-[4-(1H-tetrazol-5-yl)phenoxy]butoxy}-1H-indole;
1-(2-methylbenzyl-4-propyl-5-{4-[4-(1H-tetrazol-5-yl)phenoxy]butoxy}-1H-indole;
4-propyl-1-(pyridin-2-ylmethyl)-5-{4-[4-(1H-tetrazol-5-yl)phenoxy]butoxy}-1H-indole;
and pharmaceutically acceptable salts thereof.

The compounds of the present invention are potentiators of metabotropic glutamate (mGluR) receptor function, in particular they are potentiators of mGluR2 receptors. That is, the compounds of the present invention do not appear to bind at the glutamate recognition site on the mGluR receptor, but in the presence of glutamate or a glutamate agonist, the compounds of the present invention increase mGluR receptor response. The present potentiators are expected to have their effect at mGluR receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGluR2 receptor. Thus, the potentiators of the present invention are expected to be useful in the treatment of various neurological and psychiatric disorders associated with glutamate dysfunction described to be treated herein and others that can be treated by such potentiators as are appreciated by those skilled in the art.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of potentiating metabotorpic glutamate receptor activity in a patient such as a mammal in need of such inhibition comprising the administration of an effective amount of the compound. The present invention is directed to the use of the compounds disclosed herein as potentiators of metabotorpic glutamate receptor activity. In addition to primates, especially humans, a variety of other mammals can be treated according to the method of the present invention.

The present invention is further directed to a method for the manufacture of a medicament for potentiating metabotorpic glutamate receptor activity in humans and animals comprising combining a compound of the present invention with a pharmaceutical carrier or diluent.

The subject treated in the present methods is generally a mammal, preferably a human being, male or female, in whom potentiation of metabotorpic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of metabotropic glutamate receptor activity, in particular mGluR2 activity, may be demonstrated by methodology known in the art. Inhibition constants are determined as follows. The compounds of the present invention were tested in a [$^{35}$S]-GTPγS assay. The stimulation of [$^{35}$S]-GTPγS binding is a common functional assay to monitor Gαi-coupled receptor in native and recombinant receptor membrane preparation. Membrane from cells stably expressing hmGlu2 CHO-K1 (50 μg) were incubated in a 96 well plate for 1 hour in the presence of GTPγS$^{35}$ (0.05 nM), GDP (5 μM) and compounds. The reaction was stopped by rapid filtration over Unifilter GF/B plate (Packard, Bioscience, Meriden Conn.) using a 96-well cell harvester (Brandel Gaithersburg, Md.). The filter plates were counted using Topcount counter (Packard, Bioscience, Meriden Conn., USA). When compounds were evaluated as potentiator they were tested in the presence of glutamate (1 μM). The activation (agonist) or the potentiation of glutamate (potentiator) curves were fitted with a four parameters logistic equation giving $EC_{50}$ and Hill coefficient using the iterative non linear curve fitting software GraphPad (San Diego Calif., USA).

In particular, the compounds of the following examples had activity in potentiating the mGluR2 receptor in the aforementioned assays, generally with an $EC_{50}$ of less than about 10 μM. Preferred compounds within the present invention had activity in potentiating the mGluR2 receptor in the aforementioned assays with an $EC_{50}$ of less than about 1 μM. Such a result is indicative of the intrinsic activity of the compounds in use as potentiators of mGluR2 receptor activity.

Metabotropic glutamate receptors including the mGluR2 receptor have been implicated in a wide range of biological functions. This has suggested a potential role for these receptors in a variety of disease processes in humans or other species.

The compounds of the present invention have utility in treating, preventing, ameliorating, controlling or reducing the risk of a variety of neurological and psychiatric disorders associated with glutamate dysfunction, including one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Of the disorders above, the treatment of migraine, anxiety, schizophrenia, and epilepsy are of particular importance. In a preferred embodiment the present invention provides a method for treating migraine, comprising: administering to a patient in need thereof an effective amount of a compound of formula I. In another preferred embodiment the present invention provides a method for preventing or treating anxiety, comprising: administering to a patient in need thereof an effective amount of a compound of formula I. Particularly preferred anxiety disorders are generalized anxiety disorder, panic disorder, and obsessive compulsive disorder. In another preferred embodiment the present invention provides a method for treating schizophrenia, comprising: administering to a patient in need thereof an effective amount of a compound of formula I. In yet another preferred embodiment the present invention provides a method for treating epilepsy, comprising: administering to a patient in need thereof an effective amount of a compound of formula I.

Of the neurological and psychiatric disorders associated with glutamate dysfunction which are treated according to the present invention, the treatment of migraine, anxiety, schizophrenia, and epilepsy are particularly preferred. Particularly preferred anxiety disorders are generalized anxiety disorder, panic disorder, and obsessive compulsive disorder.

Thus, in a preferred embodiment the present invention provides a method for treating migraine, comprising: administering to a patient in need thereof an effective amount of a compound of formula I or a pharmaceutical composition thereof. In one of the available sources of diagnostic tools, Dorland's Medical Dictionary (23'd Ed., 1982, W. B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another preferred embodiment the present invention provides a method for treating anxiety, comprising: administering to a patient in need thereof an effective amount of a compound of formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment the present invention provides a method for treating depression, comprising: administering to a patient in need thereof an effective amount of a compound of formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-IV.

In another preferred embodiment the present invention provides a method for treating epilepsy, comprising: administering to a patient in need thereof an effective amount of a compound of formula I or a pharmaceutical composition thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized non-convulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

The subject compounds are further useful in a method for the prevention, treatment, control, amelioration, or reducation of risk of the diseases, disorders and conditions noted herein.

The subject compounds are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provided the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of formula I, a number of factors are considered by the attending diagnostician, including, but not limited to: the mGluR agonist selected to be administered, including its potency and selectivity; the compound of formula I to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleageneous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared in a variety of fashions.

SCHEME 1

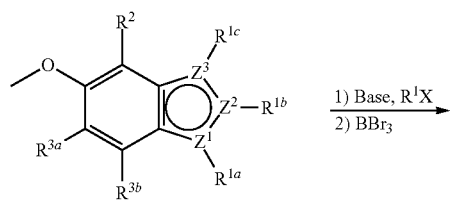

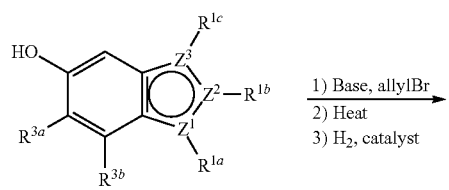

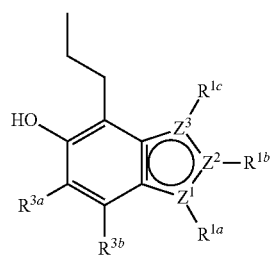

The benzazole headpiece of a given compound can be prepared as outlined in Scheme 1. A substituted methoxy-benzazole (either purchased commercially or prepared using techniques well known in the art) is reacted with $R^1X$ in the presence of a base (sodium hydride or the like) in a suitable solvent such as tetrahydrofuran or N, N-dimethylformamide. This reaction is generally run at ambient temperature to 70° C. for a period of 4 to 24 hours. The methyl ether can be subsequently removed by treatment with boron tribromide in a suitable solvent such as dichloromethane. This reaction is generally run at 0° C. to ambient temperature for a period of 1 to 8 hours. The product from each reaction can be isolated and purified employing standard techniques such as solvent extraction, chromatography, crystallization, distillation and the like.

Compounds where $R^2$=allyl or propyl can be prepared from substituted hydroxy-benzazoles (either purchased commercially or prepared using techniques well known in the art; including that described above). The hydroxyl group is first allylated with allyl bromide in the presence of a base (potassium carbonate or the like) in a suitable solvent such as acetone or N,N-dimethylformamide. This reaction is generally run at ambient temperature to 70° C. for a period of 1 to 48 hours. The product is then converted to the C-allyl derivative by thermolysis in a suitable solvent such as bromobenzene or diphenyl ether. This reaction is generally run at 150° C. to 200° C. for a period of 4 to 24 hours. The C-allyl compound can then be converted to the propyl compound by exposure to hydrogen gas in the presence of a catalyst (Pd/C or the like) in a suitable solvent such as ethyl acetate or ethanol. This reaction is generally run at ambient temperature for a period of 0.5 to 6 hours. The product from each reaction can be isolated and purified employing standard techniques such as solvent extraction, chromatography, crystallization, distillation and the like.

SCHEME 2

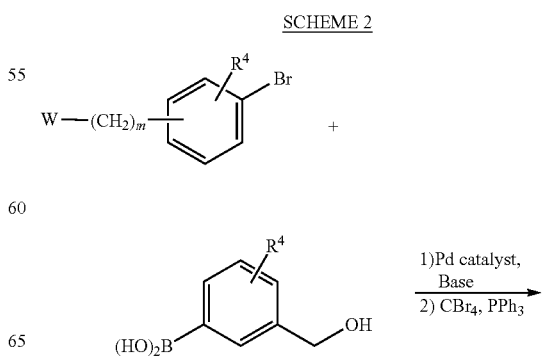

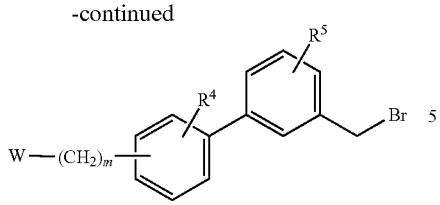

The left-hand portion of compounds where X is a substituted phenyl group can be prepared as outlined in Scheme 2. A substituted aryl bromide (either purchased commercially or prepared using techniques well known in the art) and a substituted 3-(hydroxymethyl)-phenylboronic acid (either purchased commercially or prepared using techniques well known in the art) are coupled with a palladium catalyst (PdCl$_2$ (PPh$_3$)$_2$ or the like) in the presence of a base (potassium carbonate or the like) in a suitable solvent such as toluene/methanol. This reaction is generally run at 60° C. to 100° C. for a period of 4 to 24 hours. The product is then converted to the corresponding bromide by treatment with carbon tetrabromide and triphenylphosphine in a suitable solvent such as dichloromethane. This reaction is generally run at 0° C. to ambient temperature for a period of 0.5 to 4 hours. The product from each reaction can be isolated and purified employing standard techniques such as solvent extraction, chromatography, crystallization, distillation and the like.

SCHEME 3

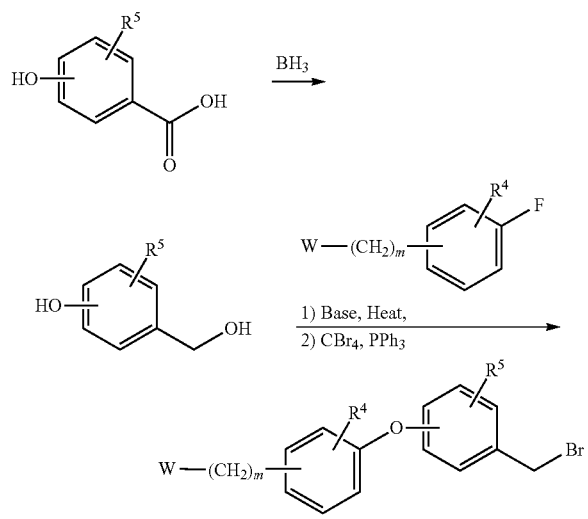

The left-hand portion of compounds where X is a substituted phenoxy group can be prepared as outlined in Scheme 3. A substituted aryl fluoride (either purchased commercially or prepared using techniques well known in the art) and a substituted (hydroxymethyl)phenol (either purchased commercially or prepared using techniques well known in the art; including borane reduction of the corresponding acid) are coupled in the presence of a base (potassium carbonate or the like) in a suitable solvent such as N, N-dimethylformamide. This reaction is generally run at 100° C. to 160° C. for a period of 3 to 12 hours. The product is then converted to the corresponding bromide by treatment with carbon tetrabromide and triphenylphosphine in a suitable solvent such as dichloromethane. This reaction is generally run at 0° C. to ambient temperature for a period of 0.5 to 4 hours. The product from each reaction can be isolated and purified employing standard techniques such as solvent extraction, chromatography, crystallization, distillation and the like.

SCHEME 4

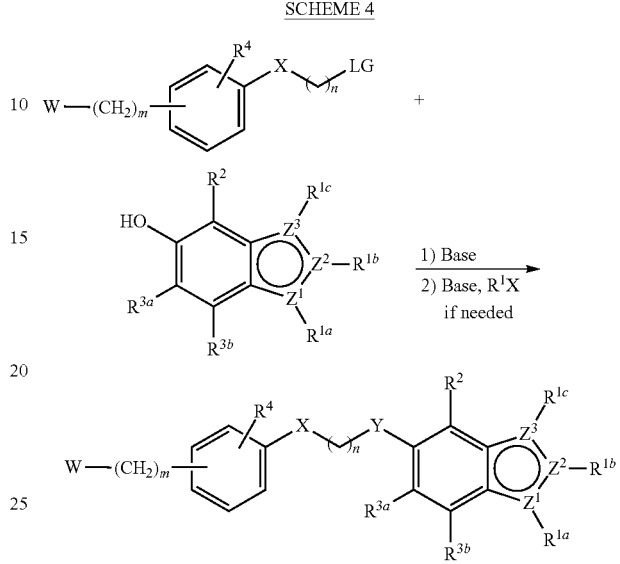

An appropriately substituted benzazole compound where A=phenyl can be prepared as outlined in Scheme 4. A substituted benzazole headpiece (prepared as in Scheme 1) is alkylated with variously substituted aryl compounds. These aryl compounds contain alkyl, cycloalkyl, alkenyl, benzyl, and heterocycloalkyl linkers with a suitable leaving group (halide, mesylate, or the like) and are reacted in the presence of a base (potassium carbonate or the like) in a suitable solvent such as tetrahydrofuran or N,N-dimethylformamide. This reaction is generally run at ambient temperature to 70° C. for a period of 4 to 24 hours. The product of the reaction can be further alkylated with R$^1$X as described for Scheme 1. The product from each reaction can be isolated and purified employing standard techniques such as solvent extraction, chromatography, crystallization, distillation and the like.

SCHEME 5

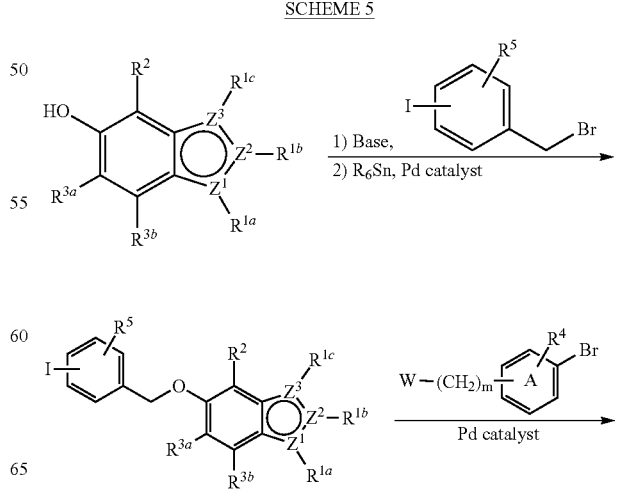

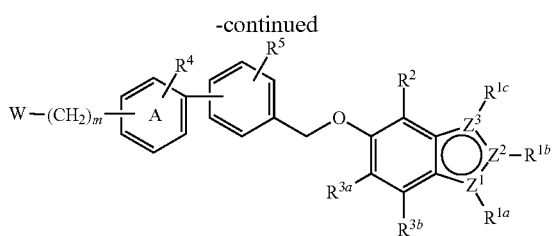

An appropriately substituted benzazole compound where A=pyridyl can be prepared as outlined in Scheme 5. A substituted benzazole headpiece (prepared as in Scheme 1) is alkylated with a substituted iodobenzyl bromide in the presence of a base (potassium carbonate or the like) in a suitable solvent (tetrahydrofuran, N,N-dimethylformamide, or the like). This reaction is generally run at ambient temperature to 40° C. for a period of 1 to 8 hours. Subsequently, the aryl iodide is converted to the aryltrialkyltin species. This reaction is carried out with a palladium catalyst (Pd(PPh₃)₄ or the like) in the presence of hexamethylditin or the like in a suitable solvent such as tetrahydrofuran and is generally run at 40° C. to 100° C. for a period of 4 to 24 hours. Next, the aryltrialkyltin and a substituted bromopyridine (either purchased commercially or prepared using techniques well known in the art) are coupled with a palladium catalyst (Pd(PPh₃)₄ or the like) in a suitable solvent such as toluene. This reaction is generally run at 80° C. to 120° C. for a period of 8 to 48 hours. The product from each reaction can be isolated and purified employing standard techniques such as solvent extraction, chromatography, crystallization, distillation and the like.

SCHEME 6

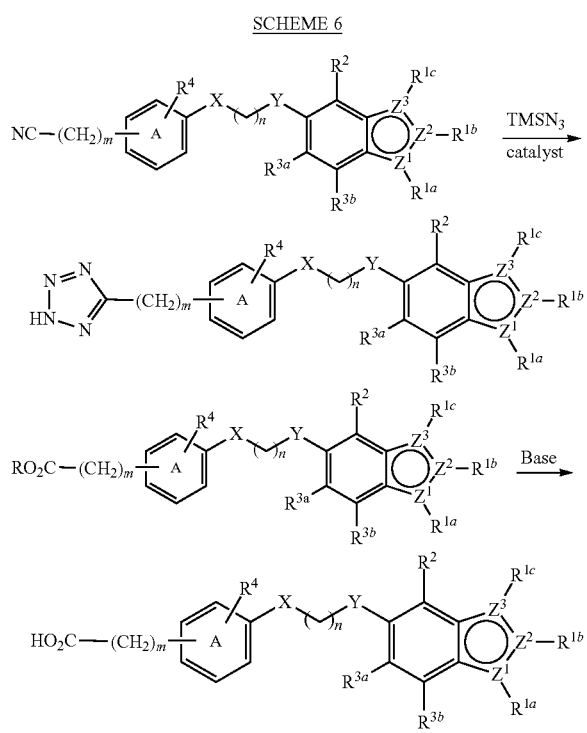

The benzazole compounds where W=CN or CO₂R can be converted into tetrazoles or acids, respectively as shown in Scheme 6. The nitrile compounds are reacted with trimethylsilyl azide in the presence of a catalyst such as dibutyltin oxide in a suitable solvent (benzene, toluene, or the like). This reaction is generally run at 80° C. to 110° C. for a period of 8 to 24 hours. The ester compounds are hydrolyzed in the presence of a suitable base (lithium hydroxide or the like) in a solvent such as tetrahydrofuran/water, tetrahydrofuran/methanol/water, or ethanol/water. This reaction is generally run at ambient temperature to 70° C. for a period of 4 to 24 hours. The product from each reaction can be isolated and purified employing standard techniques such as solvent extraction, chromatography, crystallization, distillation and the like.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

EXAMPLE 1

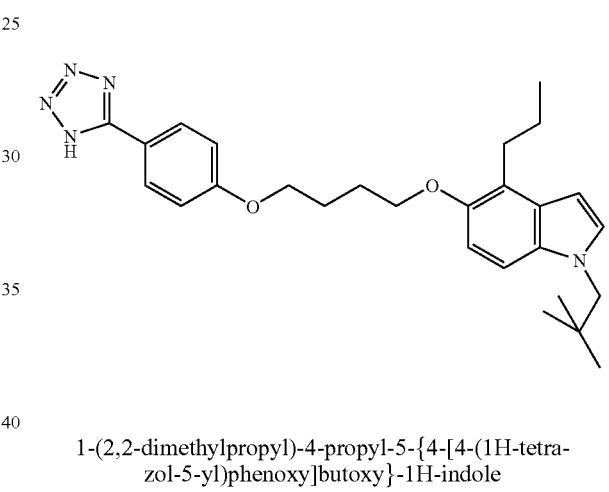

1-(2,2-dimethylpropyl)-4-propyl-5-{4-[4-(1H-tetrazol-5-yl)phenoxy]butoxy}-1H-indole 5-(Allyloxy)-1H-indole (8.0 g, 46 mmol) was added in 1 g portions to a mixture of NaH (3.5 g, 60 wt %, 88 mmol) and DMF (80 ml) at 0° C. under N₂. The reaction was allowed to warm to rt and then 1-Iodo-2,2-dimethylpropane (20 mL, 0.15 mol) was added. After stirring for 15 h, the mixture was heated at 70° C. for 8 h and then allowed to cool to rt. The reaction mixture was concentrated, diluted with water (200 mL), and extracted with ethyl acetate (100 mL×2). The combined organic extracts were dried (MgSO₄), filtered, and concentrated to give clear oil. MS (ESI): 244.1 (M+H). A solution of the above indole and diphenyl ether (40 mL) was heated at 190° C. for 4 h under N₂ and then allowed to cool to rt. The resulting solution was purified by silica gel chromatography (hexanes:ethyl acetate—1:0→2:1) to give an off-white solid. MS (ESI): 244.1 (M+H). The above indole, Pd/C (1.8 g, 10 wt %, 1.7 mmol Pd), and ethyl acetate (50 mL) were stirred vigorously under an atmosphere of H₂ for 3 h. The reaction mixture was filtered through Celite with ethyl acetate (100 mL) and concentrated to give 1-(2,2-dimethylpropyl)-4-propyl-1H-indol-5-ol. MS (ESI): 246.0 (M+H). A mixture of the above indole (3.0 g, 12.2 mmol), 4-(4-bromobutoxy)benzonitrile (3.4 g, 13.4 mmol), K₂CO₃ (4 g, 29 mmol), and DMF (15 mL) was heated at 90° C. under N₂-acetone can be used in place of DMF, but longer reaction times are required. After 22 h, a second aliquot of both 4-(4-bromobutoxy)benzonitrile and K₂CO₃ were added. After an additional 10 h, a third aliquot of both 4-(4-bromobutoxy)benzonitrile and K₂CO₃ were added. After an additional 12 h, the reaction was allowed to cool to rt. The resulting mixture was filtered through Celite with chloroform (100 mL), concentrated, and purified by silica gel chromatography (hexanes:ethyl acetate—1:0→3:2) to give a light brown solid. MS (ESI): 419.2 (M+H). A solution of the above indole (3.0 g, 7.2 mmol), trimethylsilylazide (10 mL, 75 mmol), dibutyltin oxide (360 mg, 1.5 mmol), and toluene (30 mL) was heated at reflux for 14 h under $N_2$ and then allowed to cool to rt. The reaction mixture was poured onto silica, washed with hexanes (300 mL), and then eluted with $CH_3OH:CHCl_3$ (1:4; 500 mL). The collected eluent was concentrated and purified by silica gel chromatography (hexanes:ethyl acetate—7:3→0:1) or reverse-phase HPLC to give a white solid. ¹H NMR (500 MHz, DMSO) δ 7.97 (d, 2H), 7.24 (d, 1H), 7.21 (d, 1H), 7.19 (d, 2H), 6.88 (d, 1H), 6.37 (d, 1H), 4.16 (t, 2H), 4.02 (t, 2H), 3.90 (s, 2H), 2.77 (t, 2H), 2.00-1.88 (m, 4H), 1.61-1.55 (m, 2H), 0.92 (s, 9H), 0.90 (t, 3H). MS (ESI): 462.1 (M+H).

EXAMPLE 2

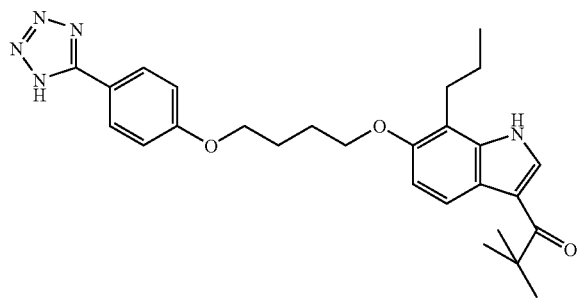

2,2-dimethyl-1-(7-propyl-6-{4-[4-(1H-tetrazol-5-yl)phenoxy]butoxy}-1H-indol-3-yl)propan-1-one A mixture of 1H-indol-6-ol (2.0 g, 15 mmol), 3-bromoprop-1-ene (1.5 mL, 17 nmol), K₂CO₃ (6.3 g, 46 mmol), and acetone (20 mL) was heated at reflux for 16 h under $N_2$ and then allowed to cool to rt. The resulting mixture was filtered through Celite with CHCl₃ (100 mL) and concentrated to give a yellow oil. MS (ESI): 173.9 (M+H). A solution of the above indole and bromobenzene (15 mL) was heated at reflux for 22 h under $N_2$ and then allowed to cool to rt. The resulting solution was purified by silica gel chromatography (hexanes:ethyl acetate—1:0→2:3) to give an off-white solid. The above indole (1.4 g, 8.2 mmol), Pd/C (85 mg, 10 wt %, 80 µmol Pd), and ethyl acetate (20 mL) were stirred vigorously under an atmosphere of $H_2$ for 30 min. The reaction mixture was filtered through Celite with ethyl acetate (100 mL) and concentrated to give a yellow oil. MS (ESI): 176.0 (M+H). The above indole was allylated with 4-(4-bromobutoxy)benzonitrile as outlined in example 1. MS (ESI): 349.2 (M+H). Diethylaluminum chloride (1.5 mL, 1 M in hexanes, 1.5 mmol) was added to a solution of the above indole (0.35 g, 1.0 mmol) and CH₂Cl₂ (10 mL) at 0° C. under $N_2$. After 30 min, 2,2-dimethylpropanoyl chloride (0.19 mL, 1.5 mmol) was added. The reaction was maintained for 6 h, quenched with pH 7 buffer (10 mL), and extracted with CHCl₃ (20 mL×3). The organic extracts were dried (MgSO₄), filtered, and concentrated to give a yellow oil. MS (ESI): 433.2 (M+H). The tetrazole-forming reaction was conducted as outlined in example 1 to give a white solid. ¹H NMR (500 MHz, DMSO) δ 11.61 (s, 1H), 8.17 (d, 1H), 8.05 (d, 1H), 7.97 (d, 2H), 7.17 (d, 2H), 6.93 (d, 1H), 4.16 (t, 2H), 4.07 (t, 2H), 2.81 (t, 2H), 1.98-1.89 (m, 4H), 1.59-1.51 (m, 2H), 1.34 (s, 9H), 0.90 (t, 3H). MS (ESI): 476 (M+H).

EXAMPLE 3

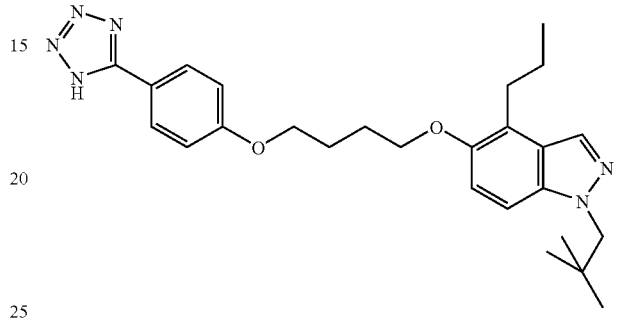

1-(2,2-dimethylpropyl)-4-propyl-5-{4-[4-(1H-tetrazol-5-yl)phenoxy]butoxy}-1H-indazole Similar procedures as outlined in examples 1 & 2 were followed using 1H-indazol-5-ol. ¹H NMR (500 MHz, DMSO) δ 8.01 (s, 1H), 7.97 (d, 2H), 7.45 (d, 1H), 7.22-7.13 (m, 3H), 4.16 (t, 2H), 4.13 (s, 2H), 4.07 (t, 2H), 2.83 (t, 2H), 2.00-1.87 (m, 4H), 1.66-1.58 (m, 2H), 0.93 (s, 9H), 0.90 (t, 3H). MS (ESI): 463.3 (M+H).

EXAMPLE 4

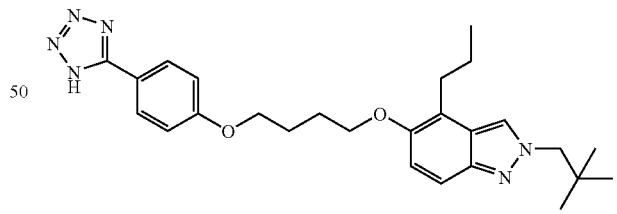

2-(2,2-dimethylpropyl)-4-propyl-5-{4-[4-(1H-tetrazol-5-yl)phenoxy]butoxy}-2H-indazole Isolated from the reaction sequence of example 3. ¹H NMR (500 MHz, DMSO) δ 8.22 (s, 1H), 7.96 (d, 2H), 7.43 (d, 1H), 7.18-7.10 (m, 3H), 4.18-4.12 (m, 5H), 4.04 (t, 2H), 2.76 (t, 2H), 1.98-1.85 (m, 4H), 1.64-1.57 (m, 2H), 0.93 (s, 9H), 0.89 (t, 3H). MS (ESI): 463.3 (M+H).

EXAMPLE 5

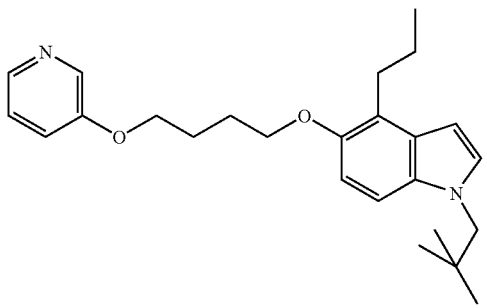

1-(2,2-dimethylpropyl)-4-propyl-5-[4-(pyridin-3-yloxy)butoxy]-1H-indole

A mixture of 1-(2,2-dimethylpropyl)-4-propyl-1H-indol-5-ol (107 mg, 0.44 mmol), 1,4-dibromobutane (1.5 mL, 12.6 mmol), $K_2CO_3$ (0.7 g, 5 mmol), and acetone (10 mL) was heated at reflux for 37 h under $N_2$ and then allowed to cool to rt. The resulting mixture was filtered through Celite with chloroform (100 mL) and concentrated to give a yellow oil. MS (ESI): 380.1 (M+H).

A mixture of the above bromide, pyridine-3-ol (66 mg, 0.69 mmol), $K_2CO_3$ (200 mg, 1.5 mmol), and acetone (10 mL) was heated at reflux for 23 h under $N_2$ and then allowed to cool to rt. The resulting mixture was filtered through Celite with chloroform (100 mL), concentrated, and purified by reverse-phase HPLC. $^1$H NMR (500 MHz, DMSO) δ 8.48 (s, 1H), 8.32 (d, 1H), 7.74 (d, 1H), 7.62-7.57 (m, 1H), 7.25 (d, 1H), 7.21 (d, 1H), 6.87 (d, 1H), 6.37 (d, 1H), 4.21 (t, 2H), 4.01 (t, 2H), 3.90 (s, 2H), 2.76 (t, 2H), 2.00-1.86 (m, 4H), 1.62-1.53 (m, 2H), 0.92 (s, 9H), 0.89 (t, 3H). MS (ESI): 395.3 (M+H).

EXAMPLE 6

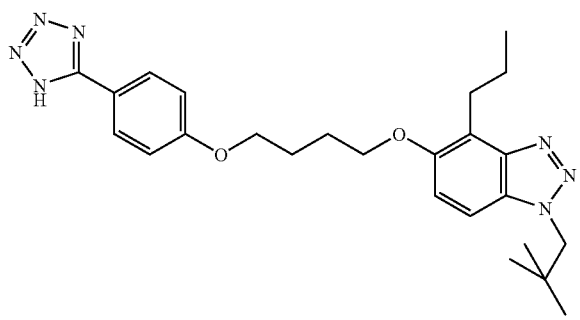

1-(2,2-dimethylpropyl)-4-propyl-5-{4-[4-(1H-tetrazol-5-yl)phenoxy]butoxy}-1H-1,2,3-benzotriazole 5-methoxy-1H-1,2,3-benzotriazole (4.0 g, 27 mmol) was added in 1 g portions to a mixture of NaH (2.2 g, 60 wt %, 55 mmol) and DMF (50 mL) at rt under $N_2$. After 15 min, 1-iodo-2,2-dimethylpropane (15 mL, 0.11 mol) was added. The mixture was heated at 60° C. for 28 h, allowed to cool to rt, concentrated, and purified by silica gel chromatography ($CHCl_3$: $CH_3OH$—1:0→19:1) to give a brown oil—a mixture of all three N-alkylated isomers. MS (ESI): 220.2 (M+H).

Boron tribromide (2.5 mL, 38 mmol) was added over 2 min to a solution of the above mixture and $CH_2Cl_2$ (60 mL) at 0° C. under $N_2$. After 8 h at 0° C., 1 N HCl (20 mL) was added slowly (internal temperature less than 30° C.). The mixture was stirred for 1 h and then concentrated to give a brown oil. MS (ESI): 206.3 (M+H).

Similar procedures as outlined in examples 1 & 2 were followed using the above mixture. $^1$H NMR (500 MHz, DMSO) δ 7.97 (d, 2H), 7.67 (d, 1H), 7.38 (d, 1H), 7.17 (d, 2H), 4.45 (s, 2H), 4.17 (t, 2H), 4.14 (t, 2H), 3.02 (t, 2H), 2.00-1.90 (m, 4H), 1.74-1.67 (m, 2H), 0.96 (s, 9H), 0.91 (t, 3H). MS (ESI): 464.3 (M+H).

EXAMPLE 7

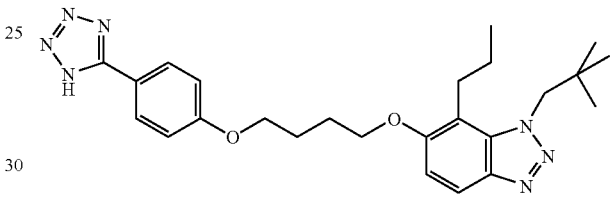

1-(2,2-dimethylpropyl)-7-propyl-6-{4-[4-(1H-tetrazol-5-yl)phenoxy]butoxy}-1H-1,2,3-benzotriazole Isolated from the reaction sequence of example 6. $^1$H NMR (500 MHz, DMSO) δ 7.97 (d, 2H), 7.86 (d, 1H), 7.35 (d, 1H), 7.17 (d, 2H), 4.48 (s, 2H), 4.21-4.15 (m, 4H), 2.96 (t, 2H), 1.99-1.93 (m, 4H), 1.55-1.48 (m, 2H), 0.95 (s, 9H), 0.93 (t, 3H). MS (ESI): 464.3 (M+H).

EXAMPLE 8

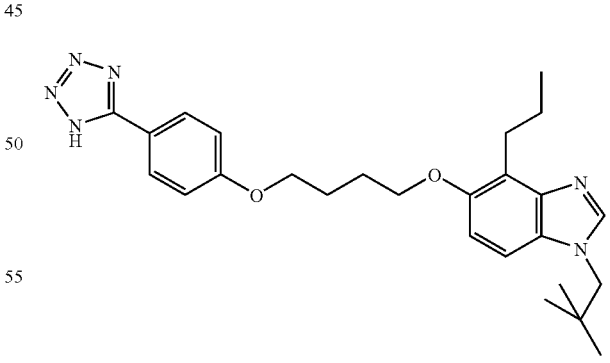

1-(2,2-dimethylpropyl)-4-propyl-5-{4-[4-(1H-tetrazol-5-yl)phenoxy]butoxy}-1H-benzimidazole A similar reaction sequence as outlined in example 6 was followed using 5-methoxy-1H-benzimidazole. $^1$H NMR (500 MHz, DMSO) δ 8.05 (s, 1H), 7.97 (d, 2H), 7.36 (d, 1H), 7.17 (d, 2H), 7.00 (d, 1H), 4.17 (t, 2H), 4.06 (t, 2H), 3.99 (s, 2H), 2.90 (t, 2H), 2.00-1.89 (m, 4H), 1.67-1.59 (m, 2H), 0.93 (s, 9H), 0.89 (t, 3H). MS (ESI): 463 (M+H).

EXAMPLE 9

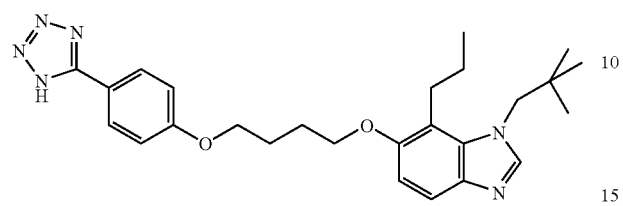

1-(2,2-dimethylpropyl)-7-propyl-6-{4-[4-(1H-tetrazol-5-yl)phenoxy]butoxy}-1H-benzimidazole Isolated from the reaction sequence of example 8. $^1$H NMR (500 MHz, DMSO) δ 7.99 (s, 1H), 7.97 (d, 2H), 7.43 (d, 1H), 7.17 (d, 2H), 6.97 (d, 1H), 4.17 (t, 2H), 4.10 (s, 2H), 4.07 (t, 2H), 2.95 (t, 2H), 1.98-1.90 (m, 4H), 1.50-1.43 (m, 2H), 0.92 (t, 3H), 0.90 (s, 9H). MS (ESI): 463 (M+H).

EXAMPLE 10

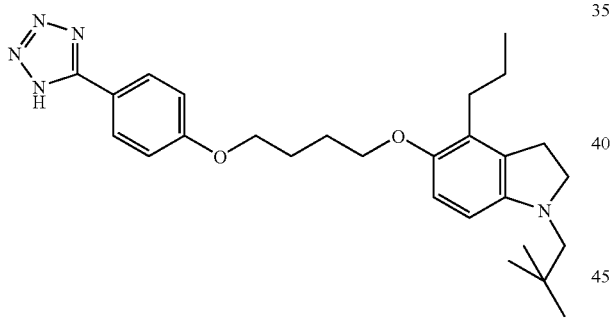

1-(2,2-dimethylpropyl)-4-propyl-5-{4-[4-(1H-tetrazol-5-yl)phenoxy]butoxy}indoline Sodium cyanoborohydride (0.50 g, 8.0 mmol) was added in four portions to a solution of 1-(2,2-dimethylpropyl)-4-propyl-1H-indol-5-ol (0.62 g, 2.5 mmol) and acetic acid (15 mL) at rt. After 45 min, water (4 mL) was added. The mixture was stirred for 15 min, concentrated, and then azeotroped with toluene (25 mL). The residue was filtered through basic alumina with ethyl acetate (150 mL) and concentrated to give a colorless foam. MS (ESI): 248.3 (M+H). Similar procedures as outlined in examples 1 were followed using the above indoline. $^1$H NMR (500 MHz, DMSO) δ 7.97 (d, 2H), 7.16 (d, 2H), 6.59 (d, 1H), 6.21 (d, 1H), 4.14 (t, 2H), 3.89 (t, 2H), 3.36 (t, 2H), 2.85 (t, 2H), 2.69 (s, 2H), 2.44 (t, 2H), 1.95-1.82 (m, 4H), 1.51-1.46 (m, 2H), 0.94 (s, 9H), 0.87 (t, 3H). MS (ESI): 464.3 (M+H).

EXAMPLE 11

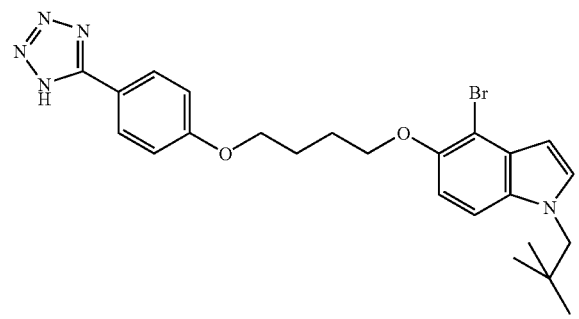

4-bromo-1-(2,2-dimethylpropyl)-5-{4-[4-(1H-tetrazol-5-yl)phenoxy]butoxy}-1H-indole Boron tribromide (0.5 mL, 5.3 mmol) was added slowly (internal temperature maintained below −50° C.) to a solution of 4-bromo-5-methoxy-1H-indole (1.0 g, 4.4 mmol) and CH$_2$Cl$_2$ (20 mL) under N$_2$. The reaction was allowed to warm to rt, and after 30 min at rt, a second aliquot of boron tribromide (1.0 mL, 11 mmol) was added. After an additional 2 h, the reaction was cooled to 0° C. and 1 N HCl (35 mL) was added slowly (internal temperature maintained below 30° C.). The mixture was stirred for 30 min and extracted with ethyl acetate (100 mL×3). The organic extracts were dried (MgSO$_4$), filtered, concentrated, and purified by silica gel chromatography (hexanes:ethyl acetate—9:1→3:2) to give a slightly red solid. MS (ESI): 212/214 (M+H). Similar procedures as outlined in example 1 were followed using the above indole. $^1$H NMR (500 MHz, DMSO) δ 7.96 (d, 2H), 7.50 (d, 1H), 7.38 (d, 1H), 7.14 (d, 2H), 7.01 (d, 1H), 6.33 (d, 1H), 4.16 (t, 2H), 4.12 (t, 2H), 3.97 (s, 2H), 2.02-1.88 (m, 4H), 0.92 (s, 9H). MS (ESI): 498/500 (M+H).

EXAMPLE 12

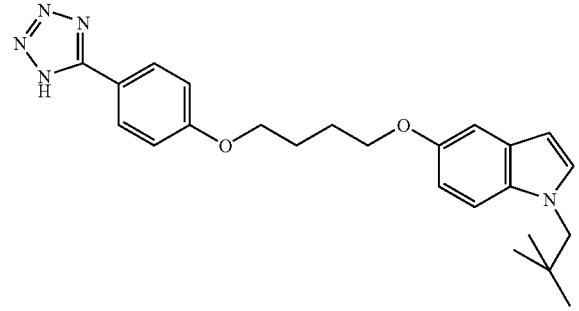

1-(2,2-dimethylpropyl)-5-{4-[4-(1H-tetrazol-5-yl)phenoxy]butoxy}-1H-indole

Similar procedures as outlined in example 1 were followed using 1H-indol-5-ol. $^1$H NMR (500 MHz, DMSO) δ 7.97 (d, 2H), 7.38 (d, 1H), 7.22 (d, 1H), 7.17 (d, 2H), 7.04 (d, 1H), 6.76 (dd, 1H), 6.32 (d, 1H), 4.15 (t, 2H), 4.03 (t, 2H), 3.92 (s, 2H), 1.96-1.86 (m, 4H), 0.91 (s, 9H). MS (ESI): 420 (M+H).

EXAMPLE 13

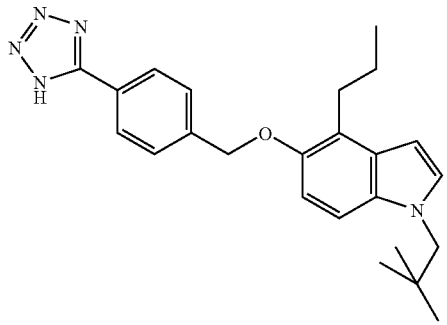

1-(2,2-dimethylpropyl)-4-propyl-5-{[4-(1H-tetrazol-5-yl)benzyl]oxy}-1H-indole

Similar procedures as outlined in example 1 were followed using 1-(2,2-dimethylpropyl)-4-propyl-1H-indol-5-ol and 4-(bromomethyl)benzonitrile. $^1$H NMR (500 MHz, DMSO) δ 8.07 (d, 2H), 7.70 (d, 2H), 7.28 (d, 1H), 7.24 (d, 1H), 6.97 (d, 1H), 6.41 (dd, 1H), 5.18 (s, 2H), 3.91 (s, 2H), 2.84 (t, 2H), 1.67-1.59 (m, 2H), 0.93 (s, 9H), 0.93 (t, 3H). MS (ESI): 404.1 (M+H).

EXAMPLE 14

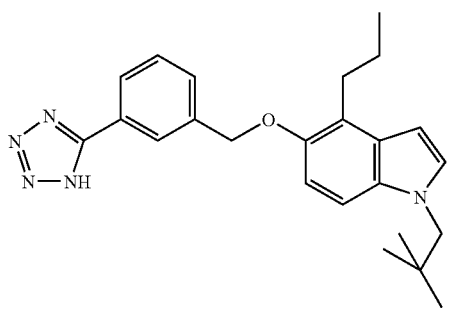

1-(2,2-dimethylpropyl)-4-propyl-5-{[3-(1H-tetrazol-5-yl)benzyl]oxy}-1H-indole

Similar procedures as outlined in example 1 were followed using 1-(2,2-dimethylpropyl)-4-propyl-1H-indol-5-ol and 3-(bromomethyl)benzonitrile. $^1$H NMR (500 MHz, DMSO) δ 8.22 (s, 1H), 7.99 (d, 1H), 7.71-7.61 (m, 2H), 7.28 (d, 1H), 7.24 (d, 1H), 6.99 (d, 1H), 6.41 (dd, 1H), 5.19 (s, 2H), 3.91 (s, 2H), 2.85 (t, 2H), 1.66-1.58 (m, 2H), 0.93 (s, 9H), 0.93 (t, 3H). MS (ESI): 404.1 (M+H).

EXAMPLE 15

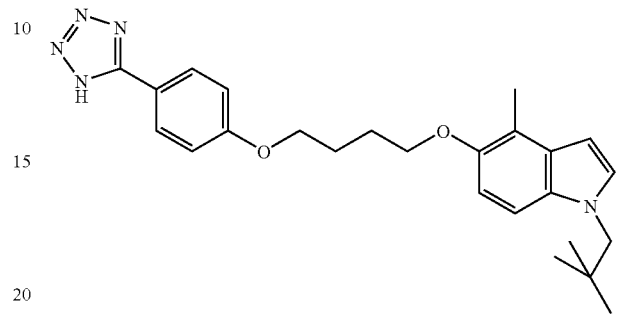

1-(2,2-dimethylpropyl)-4-methyl-5-{4-[4-(1H-tetrazol-5-yl)phenoxy]butoxy}-1H-indole Similar procedures as outlined in examples 6 were followed using 5-methoxy-4-methyl-1H-indole. $^1$H NMR (500 MHz, DMSO) δ 7.96 (d, 2H), 7.27-7.20 (m, 2H), 7.17 (d, 2H), 6.87 (d, 1H), 6.37 (d, 1H), 4.16 (t, 2H), 4.01 (t, 2H), 3.91 (s, 2H), 2.32 (s, 3H), 1.99-1.86 (m, 4H), 0.92 (s, 9H). MS (ESI): 434.1 (M+H).

EXAMPLE 16

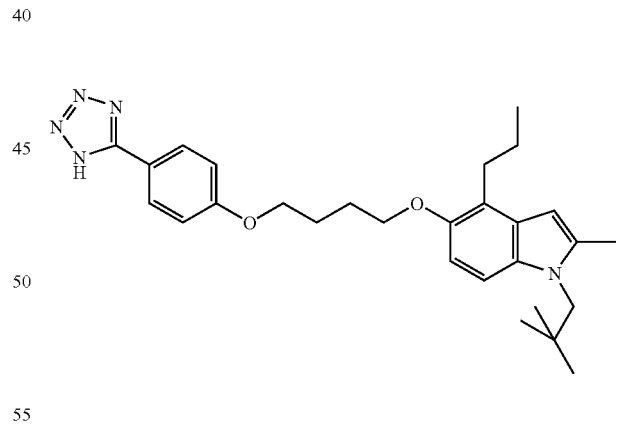

1-(2,2-dimethylpropyl)-2-methyl-4-propyl-5-{4-[4-(1H-tetrazol-5-yl)phenoxy]butoxy}-1H-indole Similar procedures as outlined in example 6 were followed using 5-methoxy-2-methyl-1H-indole. $^1$H NMR (500 MHz, DMSO) δ 7.97 (d, 2H), 7.19-7.14 (m, 3H), 6.77 (d, 1H), 6.17 (s, 1H), 4.16 (t, 2H), 4.00 (t, 2H), 3.86 (s, 2H), 2.72 (t, 2H), 2.37 (s, 3H), 1.99-1.86 (m, 4H), 1.61-1.53 (m, 2H), 0.95 (s, 9H), 0.90 (t, 3H). MS (ESI): 476.2 (M+H).

EXAMPLE 17

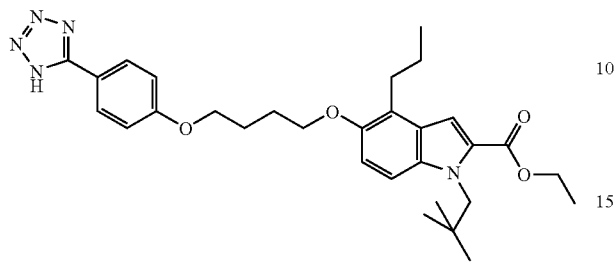

ethyl 1-(2,2-dimethylpropyl)-4-propyl-5-{4-[4-(1H-tetrazol-5-yl)phenoxy]butoxy}-1H-indole-2-carboxylate Similar procedures as outlined in example 6 were followed using ethyl 5-methoxy-1H-indole-2-carboxylate. $^1$H NMR (500 MHz, DMSO) δ 7.96 (d, 2H), 7.44 (d, 1H), 7.20-7.14 (m, 3H), 7.11 (d, 1H), 4.50 (br s, 2H), 4.30 (q, 2H), 4.17 (t, 2H), 4.06 (t, 2H), 2.80 (t, 2H), 1.99-1.87 (m, 4H), 1.62-1.54 (m, 2H), 1.32 (t, 3H), 0.91 (t, 3H), 0.83 (s, 9H). MS (ESI): 534.1 (M+H).

EXAMPLE 18

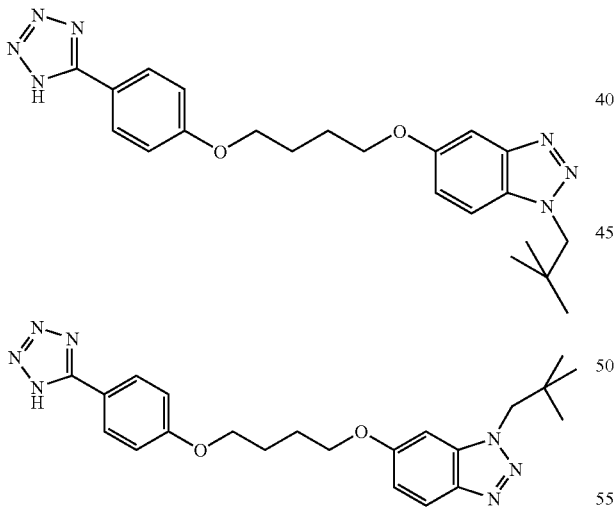

1-(2,2-dimethylpropyl)-5-{4-[4-(1H-tetrazol-5-yl)phenoxy]butoxy}-1H-1,2,3-benzotriazole and 1-(2,2-dimethylpropyl)-6-{4-[4-(1H-tetrazol-5-yl)phenoxy]butoxy}-1H-1,2,3-benzotriazole Similar procedures as outlined in example 6 were followed using 5-methoxy-1H-1,2,3-benzotriazole. $^1$H NMR (500 MHz, DMSO) δ 7.97 (d, 4.6H), 7.87 (d, 1.3H), 7.78 (d, 1H), 7.45 (d, 1H), 7.35 (d, 1.3H), 7.20-7.14 (m, 5.6H), 7.01 (d, 1.3H), 4.46 (s, 2H), 4.43 (s, 2.6H), 4.20-4.12 (m, 9.2H), 2.00-1.90 (m, 9.2H), 0.97 (s, 11.7H), 0.95 (s, 9H). MS (ESI): 422.1 (M+H).

EXAMPLE 19

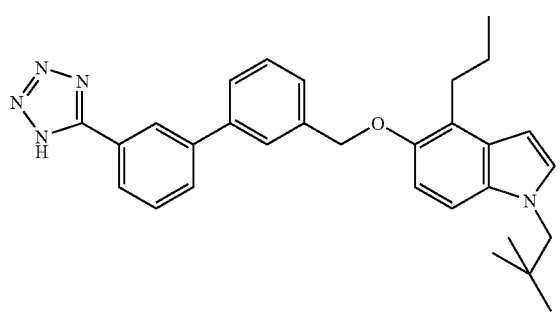

1-(2,2-dimethylpropyl)-4-propyl-5-{[3'-(1H-tetrazol-5-yl)biphenyl-3-yl]methoxy}-1H-indole Similar procedures as outlined in example 1 were followed using 1-(2,2-dimethylpropyl)-4-propyl-1H-indol-5-ol and 3'-(bromomethyl)biphenyl-3-carbonitrile. $^1$H NMR (500 MHz, DMSO) δ 8.37 (s, 1H), 8.06 (d, 1H), 7.93-7.85 (m, 2H), 7.75-7.69 (m, 2H), 7.60-7.51 (m, 2H), 7.28 (d, 1H), 7.23 (d, 1H), 7.01 (d, 1H), 6.40 (d, 1H), 5.19 (s, 2H), 3.91 (s, 2H), 2.84 (t, 2H), 1.67-1.59 (m, 2H), 0.93 (s, 9H), 0.90 (t, 3H). MS (ESI): 480.1 (M+H).

EXAMPLE 20

1-(2,2-dimethylpropyl)-4-propyl-5-{[4'-(2H-tetrazol-5-yl)biphenyl-3-yl]methoxy}-1H-indole Similar procedures as outlined in example 1 were followed using 1-(2,2-dimethylpropyl)-4-propyl-1H-indol-5-ol and 3'-(bromomethyl)biphenyl-4-carbonitrile. $^1$H NMR (500 MHz, DMSO) δ 8.15 (d, 2H), 7.93 (d, 2H), 7.87 (s, 1H), 7.72 (d, 1H), 7.57-7.51 (m, 2H), 7.28 (d, 1H), 7.23 (d, 1H), 7.01 (d, 1H), 6.40 (d, 1H), 5.18 (s, 2H), 3.91 (s, 2H), 2.84 (t, 2H), 1.67-1.59 (m, 2H), 0.93 (s, 9H), 0.93 (t, 3H). MS (ESI): 480.1 (M+H).

EXAMPLE 21

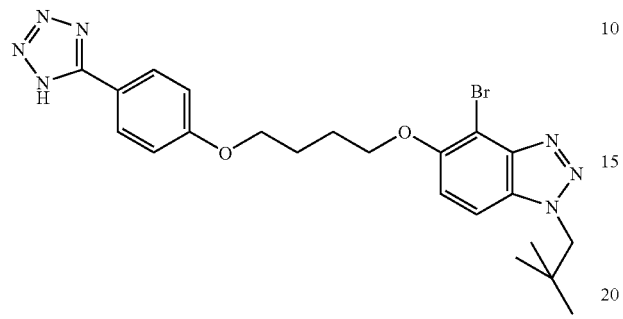

4-bromo-1-(2,2-dimethylpropyl)-5-{4-[4-(1H-tetrazol-5-yl)phenoxy]butoxy}-1H-1,2,3-benzotriazole Bromine (60 μL, 1.2 mmol) was added to a solution of 1-(2,2-dimethylpropyl)-1H-1,2,3-benzotriazol-6-ol & 1-(2,2-dimethylpropyl)-1H-1,2,3-benzotriazol-5-ol (0.22 g, 1.1 mmol), prepared as a 1.3:1.0 mixture according to example 6, and acetic acid (10 mL) at rt. After 1 h, the reaction was concentrated and purified by silica gel chromatography to give 7-bromo-1-(2,2-dimethylpropyl)-1H-1,2,3-benzotriazol-6-ol and 4-bromo-1-(2,2-dimethylpropyl)-1H-1,2,3-benzotriazol-5-ol. MS (ESI): 284/286 (M+H). Similar procedures as outlined in example 1 were followed using 4-bromo-1-(2,2-dimethylpropyl)-1H-1,2,3-benzotriazol-5-ol. $^1$H NMR (500 MHz, DMSO) δ 7.96 (d, 2H), 7.92 (d, 1H), 7.52 (d, 1H), 7.16 (d, 2H), 4.50 (s, 2H), 4.26 (t, 2H), 4.18 (t, 2H), 2.02-1.91 (m, 4H), 0.96 (s, 9H). MS (ESI): 500/502 (M+H).

EXAMPLE 22

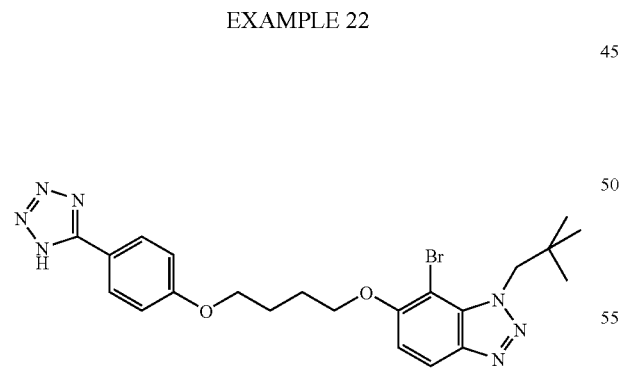

7-bromo-1-(2,2-dimethylpropyl)-6-{4-[4-(1H-tetrazol-5-yl)phenoxy]butoxy}-1H-1,2,3-benzotriazole Similar procedures as outlined in example 1 were followed using 7-bromo-1-(2,2-dimethylpropyl)-1H-1,2,3-benzotriazol-6-ol from example 21. $^1$H NMR (500 MHz, DMSO) δ 8.07 (d, 1H), 7.95 (d, 2H), 7.36 (d, 1H), 7.15 (d, 2H), 4.81 (s, 2H), 4.29 (t, 2H), 4.18 (t, 2H), 2.02-1.93 (m, 4H), 0.96 (s, 9H). MS (ESI): 500/502 (M+H).

EXAMPLE 23

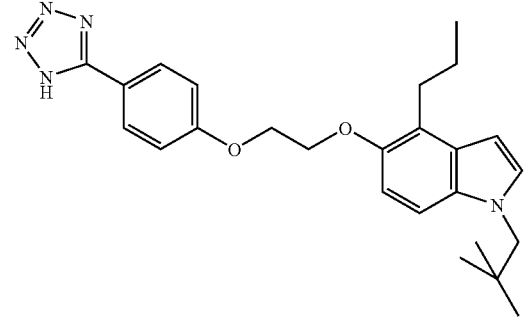

1-(2,2-dimethylpropyl)-4-propyl-5-{2-[4-(1H-tetrazol-5-yl)phenoxy]ethoxy}-1H-indole Similar procedures as outlined in example 1 were followed using 1-(2,2-dimethylpropyl)-4-propyl-1H-indol-5-ol and 4-(2-bromoethoxy)benzonitrile. $^1$H NMR (500 MHz, DMSO) δ 7.99 (d, 2H), 7.28 (d, 1H), 7.25-7.19 (m, 3H), 6.94 (d, 1H), 6.38 (d, 1H), 4.40 (t, 2H), 4.32 (t, 2H), 3.91 (s, 2H), 2.76 (t, 2H), 1.61-1.53 (m, 2H), 0.93 (s, 9H), 0.87 (t, 3H). MS (ESI): 434.1 (M+H).

EXAMPLE 24

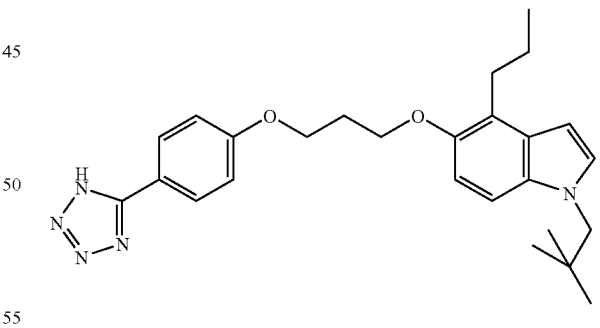

1-(2,2-dimethylpropyl)-4-propyl-5-{3-[4-(1H-tetrazol-5-yl)phenoxy]propoxy}-1H-indole Similar procedures as outlined in example 1 were followed using 1-(2,2-dimethylpropyl)-4-propyl-1H-indol-5-ol and 4-(3-bromopropoxy)benzonitrile. $^1$H NMR (500 MHz, DMSO) δ 7.98 (d, 2H), 7.25 (d, 1H), 7.23-7.16 (m, 3H), 6.89 (d, 1H), 6.37 (d, 1H), 4.30 (t, 2H), 4.12 (t, 2H), 3.90 (s, 2H), 2.75 (t, 2H), 2.24-2.18 (m, 2H), 1.59-1.51 (m, 2H), 0.92 (s, 9H), 0.86 (t, 3H). MS (ESI): 448.1 (M+H).

EXAMPLE 25

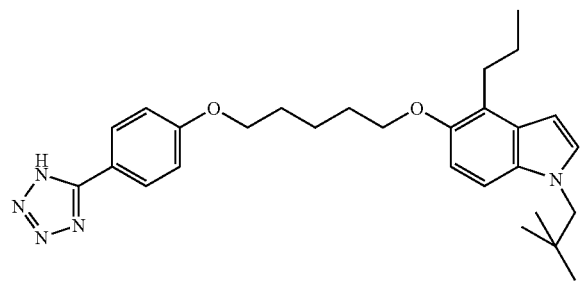

1-(2,2-dimethylpropyl)-4-propyl-5-({5-[4-(1H-tetrazol-5-yl)phenoxy]pentyl}oxy)-1H-indole Similar procedures as outlined in example 1 were followed using 1-(2,2-dimethylpropyl)-4-propyl-1H-indol-5-ol and 4-[(5-bromopentyl)oxy]benzonitrile. $^1$H NMR (500 MHz, DMSO) δ 7.96 (d, 2H), 7.23 (d, 1H), 7.21 (d, 1H), 7.15 (d, 2H), 6.86 (d, 1H), 6.37 (d, 1H), 4.10 (t, 2H), 3.97 (t, 2H), 3.89 (s, 2H), 2.77 (t, 2H), 1.88-1.76 (m, 4H), 1.69-1.53 (m, 4H), 0.92 (s, 9H), 0.91 (t, 3H). MS (ESI): 476.1 (M+H).

EXAMPLE 26

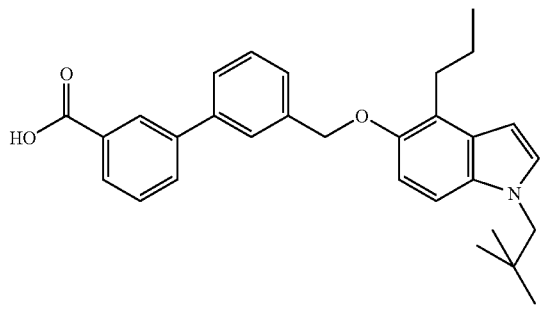

3'-({[1-(2,2-dimethylpropyl)-4-propyl-1H-indol-5-yl]oxy}methyl)biphenyl-3-carboxylic aci A mixture of ethyl-3-bromobenzoate (3.0 g, 13 mmol), [3-(hydroxymethyl)-phenyl]boronic acid (3.0 g, 20 mmol), PdCl$_2$(PPh$_3$)$_2$ (0.46 g, 0.66 mmol), K$_2$CO$_3$ (3.6 g, 26 mmol), methanol (4 mL), and toluene (36 mL) was heated at 80° C. for 18 h under N$_2$ and then allowed to cool to rt. The reaction mixture was filtered through Celite and then poured into a mixture of ethyl acetate and brine. The two layers were separated and the aqueous layer was extracted with ethyl acetate (×3). The organic extracts were dried (Na$_2$SO$_4$), filtered, concentrated and purified by silica gel chromatography to give ethyl 3'-(hydroxymethyl)biphenyl-3-carboxylate as an orange oil. A solution of CBr$_4$ (5.8 g, 17 mmol) and CH$_2$Cl$_2$ (20 mL) was added dropwise to a solution of the above alcohol, PPh$_3$ (4.6 g, 18 mmol), and CH$_2$Cl$_2$ (50 mL) at 0° C. under N$_2$. The reaction was allowed to warm to rt, maintained for 2 h, concentrated, and purified by silica gel chromatography to give ethyl 3'-(bromomethyl)biphenyl-3-carboxylate as a clear oil. Ethyl 3'-(bromomethyl)biphenyl-3-carboxylate was used to alkylate 1-(2,2-dimethylpropyl)-4-propyl-1H-indol-5-ol following the procedure outlined in example 1. A mixture of the above indole (0.66 g, 1.4 mmol), 1 N LiOH (8 mL), and THF (8 mL) was heated at 40° C. for 2 d and then cooled to 0° C.—acetone can used in place of THF if faster reaction rates are desired. The reaction was acidified to pH=1 with conc. HCl and extracted with ethyl acetate (×3). The organic extracts were dried (Na$_2$SO$_4$), filtered, concentrated and purified by silica gel chromatography to give a yellow oil. $^1$H NMR (CDCl$_3$, 500 MHz) δ 8.39 (s, 1H), 8.11 (d, 1H), 7.85 (d, 1H), 7.76 (s, 1H), 7.59-7.48 (m, 4H), 7.12 (d, 1H), 7.05 (d, 1H), 6.96 (d, 1H), 6.46 (d, 1H), 5.16 (s, 2H), 3.84 (s, 2H), 2.95 (t, 2H), 1.76 (m, 2H), 1.01 (t, 3H), 0.99 (s, 9H). MS (ESI): 456 (M+H).

EXAMPLE 27

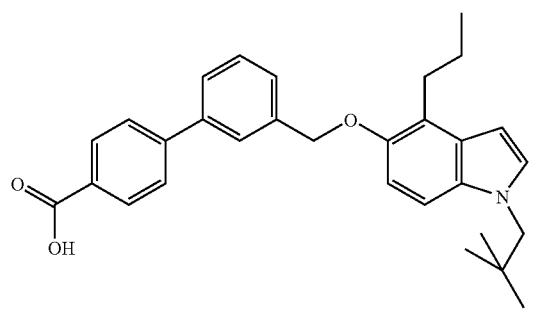

3'-({[1-(2,2-dimethylpropyl)-4-propyl-1H-indol-5-yl]oxy}methyl)biphenyl-4-carboxylic acid A similar reaction sequence as outlined in example 26 was followed using ethyl-4-bromobenzoate. $^1$H NMR (500 MHz, DMSO) δ 12.84 (br s, 1H), 8.04 (d, 2H), 7.83 (s, 1H), 7.80 (d, 2H), 7.72-7.66 (m, 1H), 7.55-7.50 (m, 2H), 7.28 (d, 1H), 7.22 (d, 1H), 7.00 (d, 1H), 6.40 (d, 1H), 5.17 (s, 2H), 3.91 (s, 2H), 2.83 (t, 2H), 1.66-1.58 (m, 2H), 0.93 (s, 9H), 0.92 (t, 3H). MS (ESI): 456.1 (M+H).

EXAMPLE 28

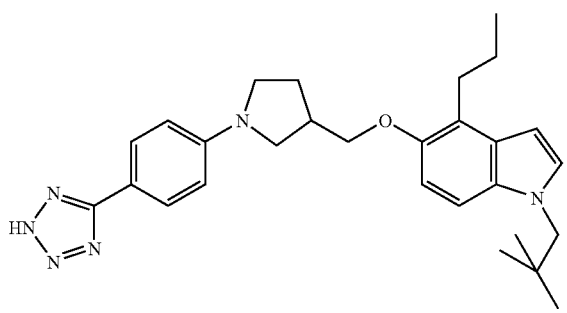

1-(2,2-dimethylpropyl)-4-propyl-5-({1-[4-(2H-tetrazol-5-yl)phenyl]pyrrolidin-3-yl}methoxy)-1H-indole A mixture of pyrrolidin-3-ylmethanol (1.0 g, 9.9 mmol), 4-fluorobenzonitrile (1.2 g, 9.9 mmol), $K_2CO_3$ (2.0 g, 14 nmol), and DMF (10 mL) was heated at 130° C. for 6 h under $N_2$ and then allowed to cool to rt. The reaction was concentrated, diluted with water (50 mL), and extracted with ethyl acetate (100 mL×3). The organic extracts were washed with brine (100 mL), dried ($MgSO_4$), filtered, and concentrated to give a brown oil. MS (ESI): 203.0 (M+H). Similar procedures as outlined in examples 26 & 1 were followed using the above alcohol. $^1$H NMR (500 MHz, DMSO) δ 7.85 (d, 2H), 7.26 (d, 1H), 7.21 (d, 1H), 6.96 (d, 1H), 6.71 (d, 2H), 6.38 (d, 1H), 4.05-3.96 (m, 2H), 3.90 (s, 2H), 3.58 (dd, 1H), 3.51-3.45 (m, 1H), 3.40 (dd, 1H), 3.29 (dd, 1H), 2.88-2.79 (m, 1H), 2.78 (t, 2H), 2.26-2.20 (m, 1H), 2.00-1.94 (m, 1H), 1.64-1.55 (m, 2H), 0.92 (s, 9H), 0.92 (t, 3H). MS (ESI): 473.1 (M+H).

EXAMPLE 29

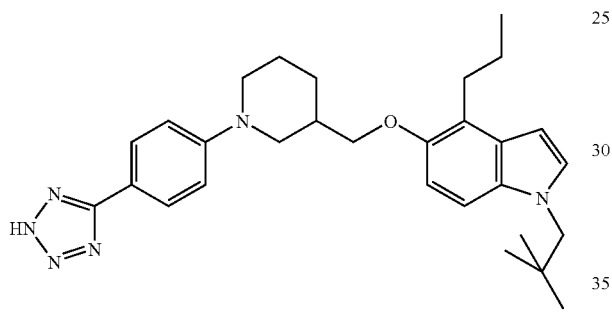

1-(2,2-dimethylpropyl)-4-propyl-5-({1-[4-(2H-tetrazol-5-yl)phenyl]piperidin-3-yl}methoxy)-1H-indole A similar reaction sequence as outlined in example 28 was followed using piperidin-3-ylmethanol. $^1$H NMR (500 MHz, DMSO) δ 7.86 (d, 2H), 7.26 (d, 1H), 7.22 (d, 1H), 7.10 (d, 2H), 6.87 (d, 1H), 6.39 (d, 1H), 4.03 (d, 1H), 3.96-3.84 (m, 5H), 2.93-2.79 (m, 4H), 2.14-2.06 (m, 1H), 1.95-1.87 (m, 1H), 1.83-1.75 (m, 1H), 1.68-1.55 (m, 3H), 1.47-1.37 (m, 1H), 0.97 (t, 3H), 0.92 (s, 9H). MS (ESI): 487.2 (M+H).

EXAMPLE 30

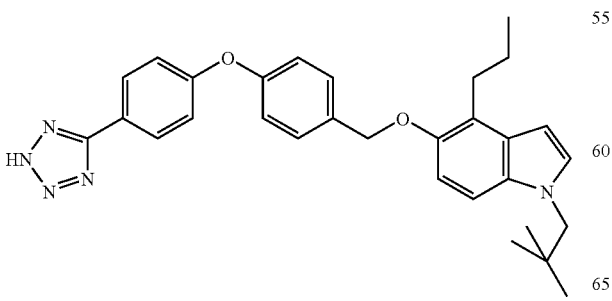

1-(2,2-dimethylpropyl)-4-propyl-5-({4-[4-(2H-tetrazol-5-yl)phenoxy]benzyl}oxy)-1H-indole A similar reaction sequence as outlined in example 28 was followed using 4-(hydroxymethyl)phenol. $^1$H NMR (500 MHz, DMSO) δ 8.05 (d, 2H), 7.55 (d, 2H), 7.28 (d, 1H), 7.23 (d, 1H), 7.21 (d, 2H), 7.17 (d, 2H), 6.99 (d, 1H), 6.40 (d, 1H), 5.08 (s, 2H), 3.92 (s, 2H), 2.82 (t, 2H), 1.65-1.56 (m, 2H), 0.93 (s, 9H), 0.92 (t, 3H). MS (ESI): 496.1 (M+H).

EXAMPLE 31

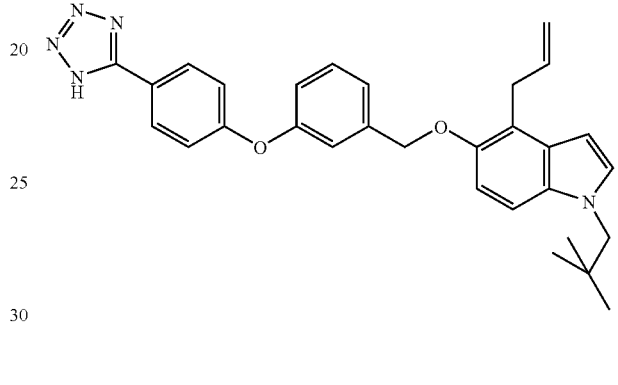

4-allyl-1-(2,2-dimethylpropyl)-5-({3-[4-(1H-tetrazol-5-yl)phenoxy]benzyl}oxy)-1H-indole A similar reaction sequence as outlined in example 28 was followed using 3-(hydroxymethyl)phenol and 4-allyl-1-(2,2-dimethylpropyl)-1H-indol-5-ol, an intermediate from example 1. $^1$H NMR (CDCl$_3$, 500 MHz) δ 7.97 (d, 2H), 7.43 (t, 1H), 7.30 (d, 1H), 7.20 (br s, 1H), 7.16 (d, 1H), 7.10 (s, 1H), 7.08 (d, 2H), 7.04-7.06 (m, 1H), 6.93 (d, 1H), 6.5 (br s, 1H), 5.90-6.03 (m, 1H), 5.10 (s, 2H), 5.05 (d, 1H), 4.95 (d, 1H), 3.90 (d, 2H), 3.68 (d, 2H), 1.00 (s, 9H).

EXAMPLE 32

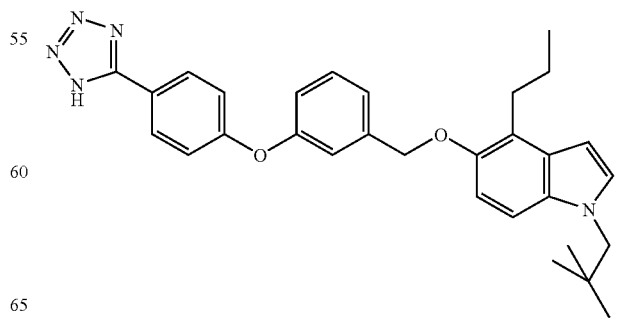

1-(2,2-dimethylpropyl)-4-propyl-5-({3-[4-(1H-tetrazol-5-yl)phenoxy]benzyl}oxy)-1H-indole The hydrogenation procedure of example 1 was followed using 4-allyl-1-(2,2-dimethylpropyl)-5-({3-[4-(1H-tetrazol-5-yl)phenoxy]benzyl}oxy)-1H-indole from example 31. MS (ESI): 496.4 (M+H).

EXAMPLE 33

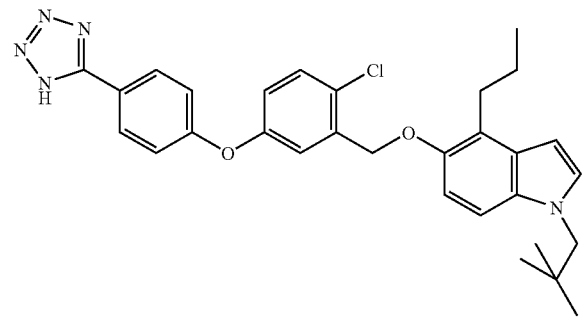

5-({2-chloro-5-[4-(1H-tetrazol-5-yl)phenoxy]benzyl}oxy)-1-(2,2-dimethylpropyl)-4-propyl-1H-indole 2-Chloro-5-hydroxybenzoic acid (3.0 g, 17 mmol) was added in three portions to a solution of $BH_3$ (50 mL, 1 M in THF, 50 mmol) at 0° C. under $N_2$. After 3 h, 1 N HCl (50 mL) was added slowly (caution: exothermic). The mixture was stirred for 30 min and extracted with ethyl acetate (150 mL×2). The organic extracts were washed with brine (100 mL), dried ($MgSO_4$), filtered, and concentrated to give a clear oil. MS (ESI): 141/143 (M−OH). A similar reaction sequence as outlined in example 28 was followed using the above alcohol. $^1$H NMR (500 MHz, DMSO) δ 8.03 (d, 2H), 7.58 (d, 1H), 7.33 (d, 1H), 7.27 (d, 1H), 7.24-7.20 (m, 3H), 7.17 (d, 1H), 6.95 (d, 1H), 6.36 (d, 1H), 5.12 (s, 2H), 3.90 (s, 2H), 2.70 (t, 2H), 1.51-1.41 (m, 2H), 0.91 (s, 9H), 0.74 (t, 3H). MS (ESI): 531/533 (M+H).

EXAMPLE 34

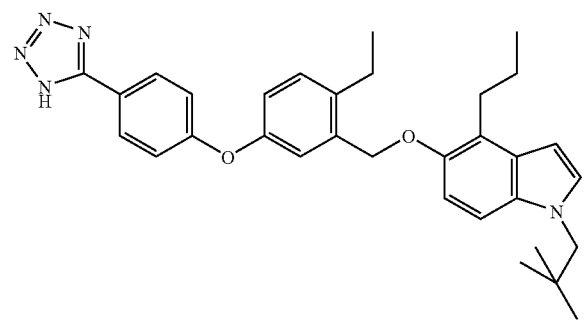

1-(2,2-dimethylpropyl)-5-({2-ethyl-5-[4-(1H-tetrazol-5-yl)phenoxy]benzyl}oxy)-4-propyl-1H-indole A similar reaction sequence as outlined in example 33 was followed using 2-ethyl-5-hydroxybenzoic acid. $^1$H NMR (500 MHz, DMSO) δ 8.01 (d, 2H), 7.34 (d, 1H), 7.26 (d, 1H), 7.24 (d, 1H), 7.21 (d, 1H), 7.15 (d, 2H), 7.07 (d, 1H), 6.99 (d, 1H), 6.36 (d, 1H), 5.10 (s, 2H), 3.90 (s, 2H), 2.77-2.67 (m, 4H), 1.53-1.43 (m, 2H), 1.24 (t, 3H), 0.91 (s, 9H), 0.77 (t, 3H). MS (ESI): 524.1 (M+H).

EXAMPLE 35

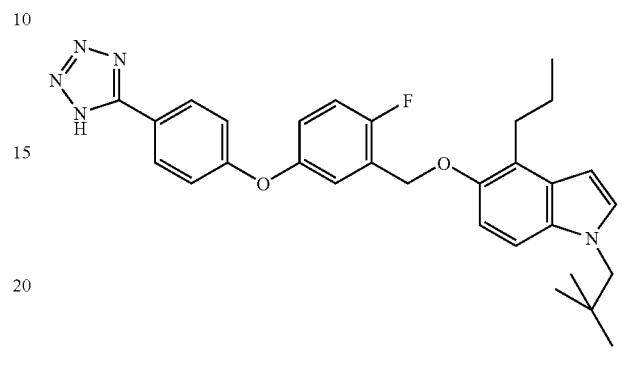

1-(2,2-dimethylpropyl)-5-({2-fluoro-5-[4-(1H-tetrazol-5-yl)phenoxy]benzyl}oxy)-4-propyl-1H-indole 4-Fluoro-3-methylphenol and 4-fluorobenzonitrile were coupled following the procedure outlined in example 28 to give 4-(4-fluoro-3-methylphenoxy)benzonitrile. A mixture of 4-(4-fluoro-3-methylphenoxy)benzonitrile (1.1 g, 4.8 mmol), N-bromosuccinimide (NBS, 1.0 g, 5.6 mmol), dibenzoyl peroxide (90 mg, 0.37 mmol), and $CCl_4$ (20 mL) was heated at reflux under $N_2$. After 1 h, a second aliquot of dibenzoyl peroxide was added. After an additional 3 h, a second aliquot of NBS and a third aliquot of dibenzoyl peroxide were added. After an additional 4 h, a fourth aliquot of dibenzoyl peroxide was added. After an additional 15 h, the reaction was allowed to cool to rt and purified by silica gel chromatography (hexanes:ethyl acetate—1:0→4:1) to give an off-white solid. MS (ESI): 306/308 (M+H). A similar reaction sequence as outlined in example 1 was followed using the above bromide and 1-(2,2-dimethylpropyl)-4-propyl-1H-indol-5-ol. $^1$H NMR (500 MHz, DMSO) δ 8.01 (d, 2H), 7.33 (t, 1H), 7.30-7.24 (m, 2H), 7.21 (d, 1H), 7.21-7.13 (m, 3H), 6.98 (d, 1H), 6.37 (d, 1H), 5.12 (s, 2H), 3.90 (s, 2H), 2.71 (t, 2H), 1.53-1.43 (m, 2H), 0.91 (s, 9H), 0.78 (t, 3H). MS (ESI): 514.2 (M+H).

EXAMPLE 36

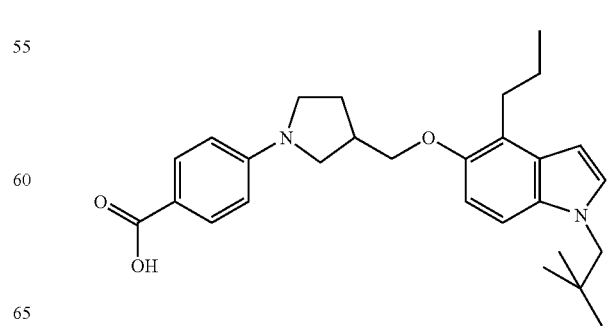

4-[3-({[1-(2,2-dimethylpropyl)-4-propyl-1H-indol-5-yl]oxy}methyl)pyrrolidin-1-yl]benzoic acid Ethyl 4-fluorobenzoate and pyrrolidin-3-ylmethanol were coupled following the procedure outlined in example 28 to give ethyl 4-[3-(hydroxymethyl)pyrrolidin-1-yl]benzoate. MS (ESI): 250.0 (M+H). A similar reaction sequence as outlined in example 26 was followed using the above alcohol. $^1$H NMR (500 MHz, DMSO) δ 12.03 (br s, 1H), 7.76 (d, 2H), 7.25 (d, 1H), 7.21 (d, 1H), 6.89 (d, 1H), 6.56 (d, 2H), 6.38 (d, 1H), 4.05-3.95 (m, 2H), 3.90 (s, 2H), 3.56 (dd, 1H), 3.49-3.42 (m, 1H), 3.38 (dd, 1H), 3.27 (dd, 1H), 2.86-2.78 (m, 1H), 2.77 (t, 2H), 2.26-2.17 (m, 1H), 2.00-1.92 (m, 1H), 1.64-1.53 (m, 2H), 0.92 (s, 9H), 0.91 (t, 3H). MS (ESI): 449.1 (M+H).

EXAMPLE 37

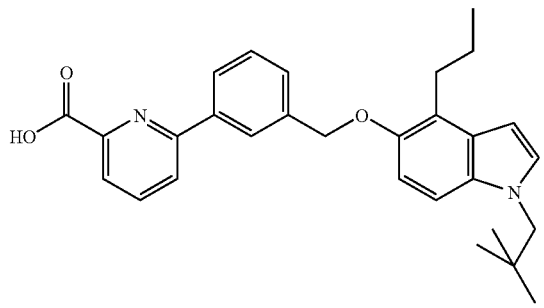

6-[3-({[1-(2,2-dimethylpropyl)-4-propyl-1H-indol-5-yl]oxy}methyl)phenyl]pyridine-2-carboxylic acid 1-(Bromomethyl)-3-iodobenzene was used to alkylate 1-(2,2-dimethyl-propyl)-4-propyl-1H-indol-5-ol following the procedure outlined in example 1. A mixture of the above indole (3.4 g, 7.3 mmol), hexamethyldistannane (5.0 g, 15 mmol), Pd(PPh$_3$)$_4$ (0.80 g, 0.69 mmol), and THF (40 mL) was heated at 60° C. for 18 h under N$_2$ and then allowed to cool to rt. The reaction mixture was diluted with water and extracted with ethyl acetate (×3). The organic extracts were dried (Na$_2$SO$_4$), filtered, concentrated, and purified by silica gel chromatography to give 1-(2,2-dimethylpropyl)-4-propyl-5-{[3-(trimethylstannyl)-benzyl]oxy}-1H-indole as a yellow oil. A mixture of the above stannane (0.35 g, 0.70 mmol), methyl 6-bromopyridine-2-carboxylate (0.22 g, 1.0 mmol), Pd(PPh$_3$)$_4$ (0.10 g, 87 μmol), and degassed toluene (10 mL) was heated at 110° C. for 24 h under N$_2$ and then allowed to cool to rt. The reaction mixture was purified by silica gel chromatography (hexanes:ethyl acetate—1:0→2:1) to give a yellow oil. MS (ESI): 471.1 (M+H). A similar procedure as outlined in example 26 was followed for the saponification of the above ester. $^1$H NMR (DMSO, 500 MHz) δ13.18 (br s, 1H), 8.31 (s, 1H), 8.19 (d, 1H), 8.12 (d, 1H), 8.09 (t, 1H), 8.01 (d, 1H), 7.61-7.53 (m, 2H), 7.28 (d, 1H), 7.23 (d, 1H), 7.00 (d, 1H), 6.40 (d, 1H), 5.19 (s, 2H), 3.91 (s, 2H), 2.84 (t, 2H), 1.68-1.58 (m, 2H), 0.93 (s, 9H), 0.91 (t, 3H). MS (ESI): 457.1 (M+H).

EXAMPLE 38

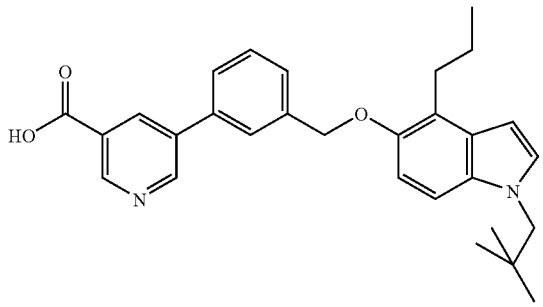

5-[3-({[1-(2,2-dimethylpropyl)-4-propyl-1H-indol-5-yl]oxy}methyl)phenyl]nicotinic acid A similar reaction sequence as outlined in example 37 was followed using methyl 5-bromonicotinate. $^1$H NMR (DMSO, 500 MHz) δ13.56 (br s, 1H), 9.12 (s, 1H), 9.07 (s, 1H), 8.49 (t, 1H), 7.89 (s, 1H), 7.80-7.72 (m, 1H), 7.59-7.55 (m, 2H), 7.28 (d, 1H), 7.23 (d, 1H), 7.00 (d, 1H), 6.40 (d, 1H), 5.19 (s, 2H), 3.91 (s, 2H), 2.84 (t, 2H), 1.68-1.58 (m, 2H), 0.93 (s, 9H), 0.92 (t, 3H). MS (ESI): 457.1 (M+H).

EXAMPLE 39

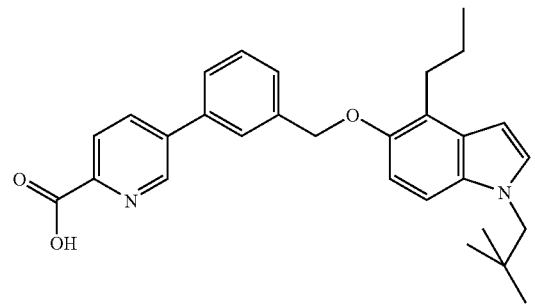

5-[3-({[1-(2,2-dimethylpropyl)-4-propyl-1H-indol-5-yl]oxy}methyl)phenyl]pyridine-2-carboxylic acid A similar reaction sequence as outlined in example 37 was followed using methyl 5-bromopyridine-2-carboxylate. $^1$H NMR (DMSO, 500 MHz) δ13.23 (br s, 1H), 9.02 (s, 1H), 8.26 (d, 1H), 8.13 (d, 1H), 7.90 (s, 1H), 7.80-7.73 (m, 1H), 7.65-7.56 (m, 2H), 7.28 (d, 1H), 7.23 (d, 1H), 7.00 (d, 1H), 6.40 (d, 1H), 5.18 (s, 2H), 3.91 (s, 2H), 2.84 (t, 2H), 1.68-1.58 (m, 2H), 0.93 (s, 9H), 0.92 (t, 3H). MS (ESI): 457.1 (M+H).

EXAMPLE 40

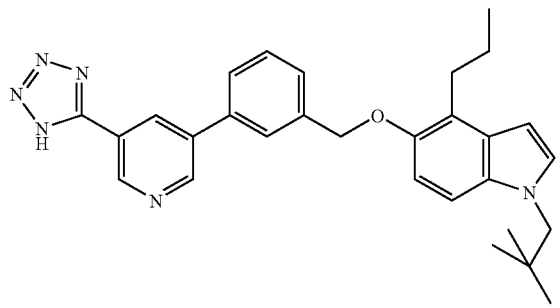

1-(2,2-dimethylpropyl)-4-propyl-5-({3-[5-(1H-tetrazol-5-yl)pyridin-3-yl]benzyl}oxy)-1H-indole A similar coupling as outlined in example 37 was followed using 5-bromonicotinonitrile. Subsequently, the tetrazole-forming reaction was conducted as outlined in example 1. $^1$H NMR (DMSO, 500 MHz) δ 9.23 (s, 1H), 9.11 (s, 1H), 8.69 (t, 1H), 7.95 (s, 1H), 7.82-7.78 (m, 1H), 7.63-7.58 (m, 2H), 7.28 (d, 1H), 7.23 (d, 1H), 7.01 (d, 1H), 6.40 (d, 1H), 5.20 (s, 2H), 3.91 (s, 2H), 2.85 (t, 2H), 1.68-1.58 (m, 2H), 0.93 (s, 9H), 0.91 (t, 3H). MS (ESI): 481.1 (M+H).

EXAMPLE 41

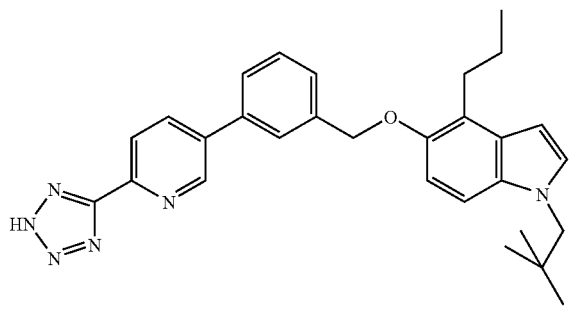

1-(2,2-dimethylpropyl)-4-propyl-5-({3-[6-(2H-tetrazol-5-yl)pyridin-3-yl]benzyl}oxy)-1H-indole A similar coupling as outlined in example 37 was followed using 5-bromopyridine-2-carbonitrile. Subsequently, the tetrazole-forming reaction was conducted as outlined in example 1. $^1$H NMR (DMSO, 500 MHz) δ 9.13 (s, 1H), 8.38 (d, 1H), 8.32 (d, 1H), 7.94 (s, 1H), 7.83-7.79 (m, 1H), 7.62-7.57 (m, 2H), 7.29 (d, 1H), 7.23 (d, 1H), 7.01 (d, 1H), 6.40 (d, 1H), 5.20 (s, 2H), 3.91 (s, 2H), 2.85 (t, 2H), 1.68-1.58 (m, 2H), 0.93 (s, 9H), 0.92 (t, 3H). MS (ESI): 481.1 (M+H).

EXAMPLE 42

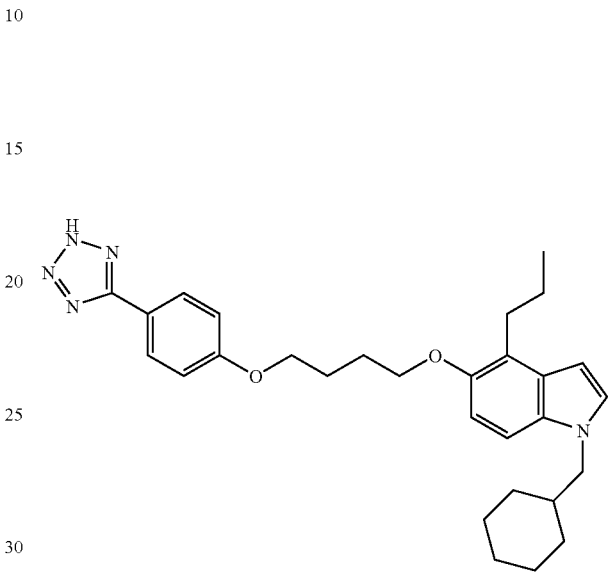

1-Cyclohexylmethyl-4-propyl-5-{4-[4-(2H-tetrazol-5-yl)-phenoxy]-butoxy}-1H-indole A mixture of K$_2$CO$_3$ (5.1 g, 37 mmol), 4-(4-bromobutoxy)benzonitrile (2.3 g, 11 mmol), 4-propyl-1H-indol-5-ol (3.5 g, 14 mmol), and acetone (53 mL) was heated at 50° C. for 48 h and then allowed to cool to rt. The resulting mixture was filtered through Celite with acetone (75 mL), concentrated, and purified by silica gel chromatography (CH$_2$Cl$_2$:CH$_3$OH—19:1→9:1) to give a pale yellow solid. $^1$H NMR (500 MHz, CDCl$_3$) δ 8.00 (s, 1H), 7.56 (d, 2H), 7.18 (m, 2H), 6.94 (d, 2H), 6.88 (d, 1H), 6.51 (d, 1H), 4.10 (t, 2H), 4.05 (t, 2H), 2.87 (t, 2H), 2.05 (m, 2H), 1.98 (m, 2H), 1.68 (m, 2H), 0.97 (t, 3H). MS (ESI): 349 (M+H). Sodium hydride (0.22 g, 95 wt %, 0.92 mmol) was added to a solution of the above indole (0.160 g 0.460 mmol) and DMF (1 mL) at 0° C. The reaction was allowed to warm to rt, stirred for 20 min, and then (bromomethyl)cyclohexane (0.162 g, 0.920 mmol) was added. After 3 h, the mixture was poured into water (10 mL) and extracted with CH$_2$Cl$_2$ (40 mL). The organic extract was washed with water (10 mL×5) and then brine (10 mL), dried (MgSO$_4$), filtered, and concentrated to give a yellow solid. MS (ESI): 445 (M+H). The tetrazole-forming reaction was conducted as outlined in example 1. $^1$H NMR (500 MHz, DMSO) δ 7.97 (d, 2H), 7.23 (d, 1H), 7.20 (d, 1H), 7.16 (d, 2H), 6.92 (d, 1H), 6.33 (d, 1H), 4.15 (t, 2H), 4.01 (t, 2H), 3.92 (d, 2H), 2.76 (t, 2H), 1.95 (m, 2H), 1.92 (m, 2H), 1.75 (m, 1H), 1.64 (m, 2H), 1.58 (m, 2H), 1.49 (d, 2H), 1.11 (m, 3H), 0.96 (m, 3H), 0.91 (t, 3H). MS (ESI): 488 (M+H).

EXAMPLE 43

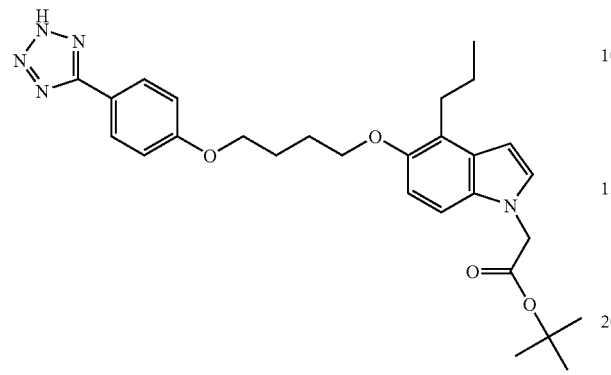

(4-Propyl-5-{4-[4-(2H-tetrazol-5-yl)-phenoxy]-butoxy}-indol-1-yl)-acetic acid tert-butyl ester A similar procedure as outlined in example 42 was followed using tert-butyl bromoacetate. $^1$H NMR (500 MHz, DMSO) δ 7.97 (d, 2H), 7.23 (d, 1H), 7.16 (d, 2H), 7.07 (d, 1H), 6.89 (d, 1H), 6.37 (d, 1H), 4.92 (s, 2H), 4.15 (t, 2H), 4.01 (t, 2H), 2.77 (t, 2H), 1.94 (m, 2H), 1.89 (m, 2H), 1.59 (m, 2H), 1.41 (s, 9H), 1.49 (t, 3H). MS (ESI): 507 (M+H).

EXAMPLE 44

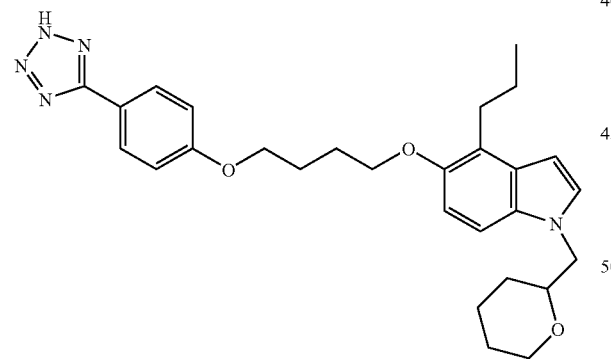

4-Propyl-1-(tetrahydro-pyran-2-ylmethyl)-5-{4-[4-(2H-tetrazol-5-yl)-phenoxy]-butoxy}-1H-indole A similar procedure as outlined in example 42 was followed using 2-(bromomethyl)tetrahydro-2H-pyran. $^1$H NMR (500 MHz, DMSO) δ 7.97 (d, 2H), 7.22 (m, 2H), 7.22 (d, 2H), 6.88 (d, 1H), 6.32 (d, 1H), 4.15 (t, 2H), 4.09 (t, 2H), 4.01 (t, 2H), 3.82 (d, 1H), 3.57 (m, 1H), 3.25 (m, 1H), 2.76 (t, 2H), 1.94 (m, 2H), 1.89 (m, 2H), 1.57 (m, 3H), 1.42 (m, 3H), 1.16 (m, 1H), 0.89 (t, 3H). MS (ESI): 490 (M+H).

EXAMPLE 45

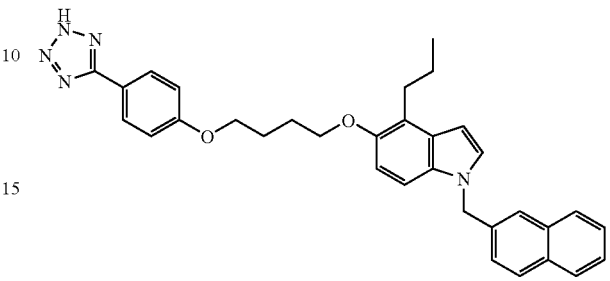

1-Naphthalen-2-ylmethyl-4-propyl-5-{4-[4-(2H-tetrazol-5-yl)-phenoxy]-butoxy}-1H-indole A similar procedure as outlined in example 42 was followed using 2-(bromomethyl)naphthalene. $^1$H NMR (500 MHz, DMSO) δ 7.96 (d, 2H), 7.85 (m, 3H), 7.76 (s, 1H), 7.49 (m, 3H), 7.34 (d, 1H), 7.25 (d, 1H), 7.15 (d, 2H), 6.85 (d, 1H), 6.44 (d, 1H), 5.51 (s, 2H), 4.14 (t, 2H), 3.98 (t, 2H), 2.78 (t, 2H), 1.92 (m, 2H), 1.88 (m, 2H), 1.59 (m, 2H), 0.90 (t, 3H). MS (ESI): 532 (M+H).

EXAMPLE 46

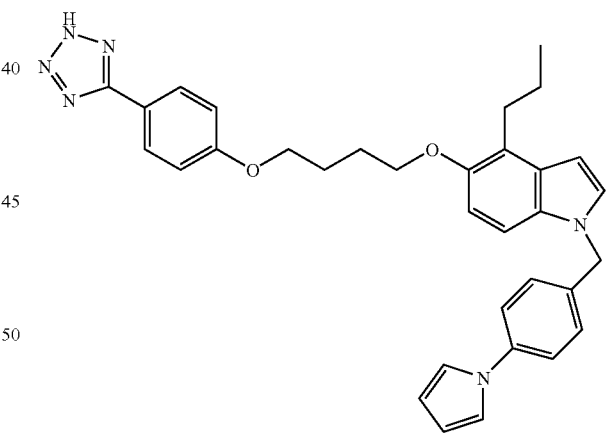

4-Propyl-1-(4-pyrrol-1-yl-benzyl)-5-{4-[4-(2H-tetrazol-5-yl)-phenoxy]-butoxy}-1H-indole A similar procedure as outlined in example 42 was followed using 1-[4-(bromomethyl)phenyl]-1H-pyrrole. $^1$H NMR (500 MHz, DMSO) δ 7.96 (d, 2H), 7.49 (d, 2H), 7.46 (d, 1H), 7.29 (d, 2H), 7.27 (d, 2H), 7.22 (d, 1H), 7.16 (d, 2H), 6.87 (d, 1H), 6.43 (d, 1H), 6.23 (t, 2H), 5.36 (s, 2H), 4.15 (t, 2H), 4.00 (t, 2H), 2.78 (t, 2H), 1.94 (m, 2H), 1.86 (m, 2H), 1.58 (m, 2H), 0.90 (t, 3H). MS (ESI): 547 (M+H).

EXAMPLE 47

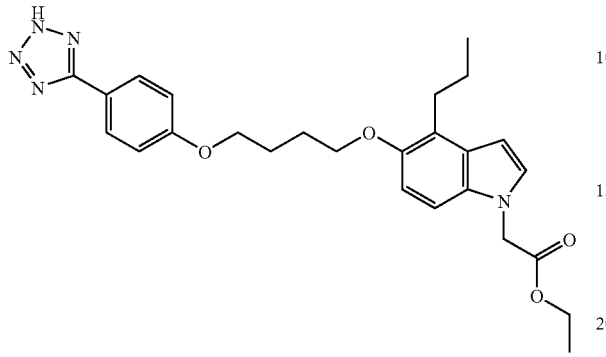

(4-Propyl-5-{4-[4-(2H-tetrazol-5-yl)-phenoxy]-butoxy}-indol-1-yl)-acetic acid ethyl ester A similar procedure as outlined in example 42 was followed using ethyl bromoacetate. $^1$H NMR (500 MHz, DMSO) δ 7.96 (d, 2H), 7.26 (d, 1H), 7.16 (d, 2H), 7.11 (d, 1H), 6.90 (d, 1H), 6.40 (d, 1H), 5.04 (s, 2H), 4.15 (m, 4H), 4.04 (t, 2H), 2.78 (t, 2H), 1.98 (m, 2H), 1.91 (m, 2H), 1.58 (m, 2H), 1.20 (t, 3H), 0.91 (t, 3H). MS (ESI): 478 (M+H).

EXAMPLE 48

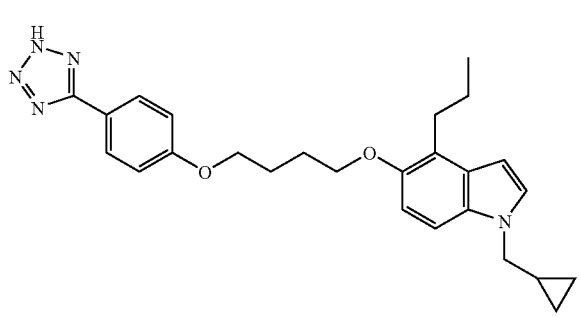

1-Cyclopropylmethyl-4-propyl-5-{4-[4-(2H-tetrazol-5-yl)-phenoxy]-butoxy}-1H-indole A similar procedure as outlined in example 42 was followed using (bromomethyl)cyclopropane. $^1$H NMR (500 MHz, DMSO) δ 7.99 (d, 2H), 7.34 (d, 1H), 7.24 (d, 1H), 7.18 (d, 2H), 6.90 (d, 1H), 6.36 (d, 1H), 4.18 (t, 2H), 4.01 (t, 2H), 3.96 (d, 2H), 2.78 (t, 2H), 1.96 (m, 2H), 1.90 (m, 2H), 1.58 (m, 2H), 1.21 (m, 1H), 0.90 (t, 3H), 0.50 (m, 2H), 0.36, (m, 2H). MS (ESI): 446 (M+H).

EXAMPLE 49

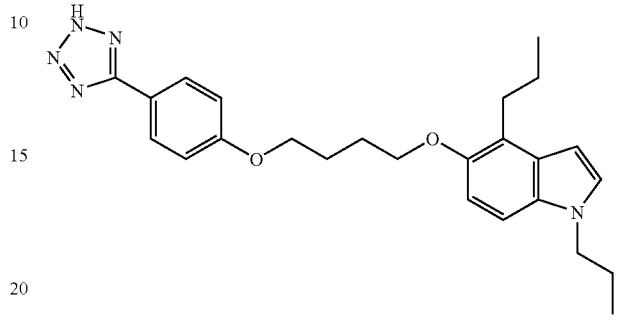

1,4-Dipropyl-5-{4-[4-(2H-tetrazol-5-yl)-phenoxy]-butoxy}-1H-indole

A similar procedure as outlined in example 42 was followed using 1-bromopropane. $^1$H NMR (500 MHz, DMSO) δ 8.00 (d, 2H), 7.28 (d, 1H), 7.21 (d, 1H), 7.18 (d, 2H), 6.90 (d, 1H), 6.35 (d, 1H), 4.18 (t, 2H), 4.05 (t, 2H), 4.02 (t, 2H), 2.78 (t, 2H), 1.75 (m, 2H), 1.61 (m, 2H), 0.91 (t, 3H), 0.84 (t, 3H). MS (ESI): 434 (M+H).

EXAMPLE 50

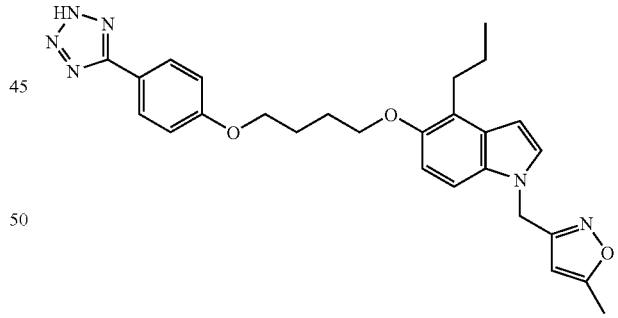

1-(5-Methyl-isoxazol-3-ylmethyl)-4-propyl-5-{4-[4-(5H-[1,2,4]triazol-3-yl)-phenoxy]-butoxy}-1H-indole A similar procedure as outlined in example 42 was followed using 3-(bromomethyl)-5-methylisoxazole. $^1$H NMR (500 MHz, DMSO) δ 7.96 (d, 2H), 7.38 (d, 1H), 7.22 (d, 1H), 7.17 (d, 2H), 6.91 (d, 1H), 6.42 (d, 1H), 5.97 (s, 1H), 5.37 (s, 2H), 4.16 (t, 2H), 4.02 (t, 2H), 2.77 (t, 2H), 2.31 (s, 3H), 1.96 (m, 2H), 1.93 (m, 2H), 1.58 (m, 2H), 0.89 (t, 3H). MS (ESI): 487 (M+H).

EXAMPLE 51

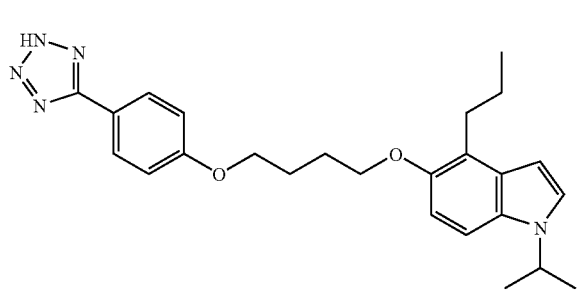

1-Isopropyl-4-propyl-5-{4-[4-(2H-tetrazol-5-yl)-phenoxy]-butoxy}-1H-indole

A similar procedure as outlined in example 42 was followed using 2-iodopropane. ¹H NMR (500 MHz, DMSO) δ 7.97 (d, 2H), 7.39 (d, 1H), 7.24 (d, 1H), 7.15 (d, 2H), 6.89 (d, 1H), 6.37 (d, 1H), 4.65 (m, 1H), 4.16 (t, 2H), 4.02 (t, 2H), 2.77 (t, 2H), 1.95 (m, 2H), 1.91 (m, 2H), 1.58 (m, 2H), 1.43 (d, 6H), 0.90 (t, 3H). MS (ESI): 434 (M+H).

EXAMPLE 52

1-(3-Methyl-butyl)-4-propyl-5-{4-[4-(2H-tetrazol-5-yl)-phenoxy]-butoxy}-1H-indole A similar procedure as outlined in example 42 was followed using 1-bromo-3-methylbutane. ¹H NMR (500 MHz, DMSO) δ 7.97 (d, 2H), 7.28 (d, 1H), 7.18 (m, 3H), 7.15 (d, 2H), 6.90 (d, 1H), 6.34 (d, 1H), 4.16 (t, 2H), 4.10 (t, 2H), 4.02

(t, 2H), 2.77 (t, 2H), 1.95 (m, 2H), 1.91 (m, 2H), 1.60 (m, 4H), 1.49 (m, 1H), 0.90 (m, 9H). MS (ESI): 462 (M+H).

EXAMPLE 53

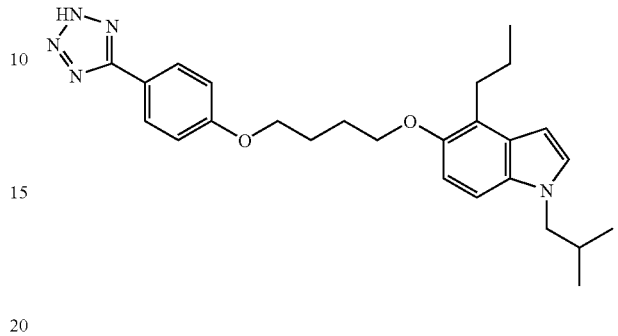

1-Isobutyl-4-propyl-5-{4-[4-(2H-tetrazol-5-yl)-phenoxy]-butoxy}-1H-indole

A similar procedure as outlined in example 42 was followed using 1-iodo-2-methylpropane. ¹H NMR (500 MHz, DMSO) δ 7.97 (d, 2H), 7.25 (d, 1H), 7.21 (d, 1H), 7.17 (d, 2H), 6.88 (d, 1H), 6.34 (d, 1H), 4.16 (t, 2H), 4.02 (t, 2H), 4.02 (t, 2H), 3.89 (d, 2H), 2.77 (t, 2H), 2.08 (m, 1H), 1.95 (m, 2H), 1.89 (m, 2H), 1.49 (m, 1H), 1.56 (m, 2H), 0.90 (t, 3H), 0.83 (d, 6H). MS (ESI): 448 (M+H).

EXAMPLE 54

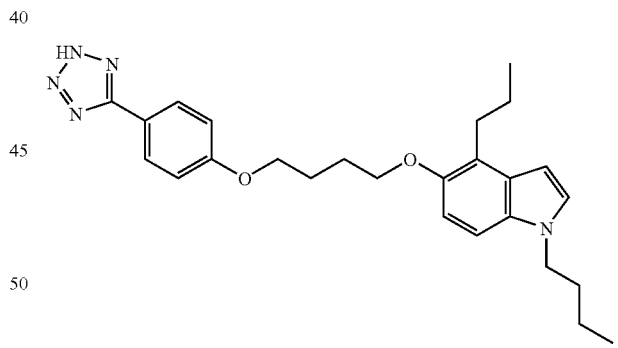

1-Butyl-4-propyl-5-{4-[4-(2H-tetrazol-5-yl)-phenoxy]-butoxy}-1H-indole

A similar procedure as outlined in example 42 was followed using 1-iodobutane. ¹H NMR (500 MHz, DMSO) δ 7.97 (d, 2H), 7.27 (d, 1H), 7.21 (d, 1H), 7.16 (d, 2H), 6.89 (d, 1H), 6.34 (d, 1H), 4.16 (t, 2H), 4.09 (t, 2H), 4.02 (t, 2H), 2.77

(t, 2H),) 1.96 (m, 2H), 1.89 (m, 2H), 1.69 (m, 2H), 1.59 (m, 2H), 0.88 (m, 6H). MS (ESI): 448 (M+H).

EXAMPLE 55

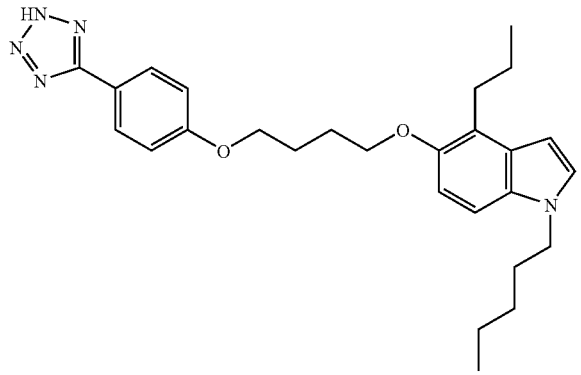

1-Pentyl-4-propyl-5-{4-[4-(2H-tetrazol-5-yl)-phenoxy]-butoxy}-1H-indole

A similar procedure as outlined in example 42 was followed using 1-iodopentane. $^1$H NMR (500 MHz, DMSO) δ 7.97 (d, 2H), 7.27 (d, 1H), 7.20 (d, 1H), 7.17 (d, 2H), 6.89 (d, 1H), 6.34 (d, 1H), 4.16 (t, 2H), 4.08 (t, 2H), 4.02 (t, 2H), 2.77 (t, 2H),) 1.95 (m, 2H), 1.90 (m, 2H), 1.72 (m, 2H), 1.58 (m, 2H), 1.29 (m, 2H), 1.21 (m, 2H), 0.89 (t, 3H), 0.84 (t, 3H). MS (ESI): 462 (M+H).

EXAMPLE 56

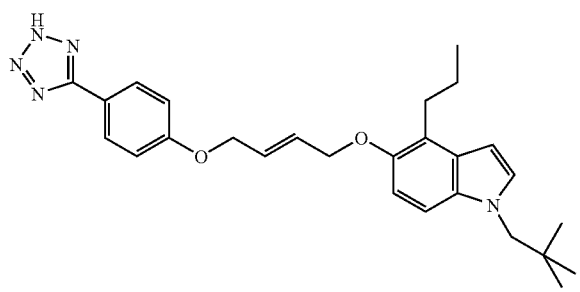

1-(2,2-Dimethyl-propyl)-4-propyl-5-{(E)-4-[4-(2H-tetrazol-5-yl)-phenoxy]-but-2-enyloxy}-1H-indole Similar procedures as outlined in example 1 were followed using 1-(2,2-dimethylpropyl)-4-propyl-1H-indol-5-ol and 4-{[(2E)-4-bromobut-2-en-1-yl]oxy}benzonitrile. $^1$H NMR (500 MHz, DMSO) δ 7.97 (d, 2H), 7.22 (d, 1H), 7.19 (d, 1H), 7.18 (d, 2H), 6.86 (d, 1H), 6.37 (d, 1H), 6.12 (m, 2H), 4.72 (d, 2H), 4.56 (d, 2H), 3.89 (s, 2H), 2.77 (t, 2H), 1.58 (m, 2H), 0.91 (s, 9H), 0.89 (t, 3H). MS (ESI): 460 (M+H).

EXAMPLE 57

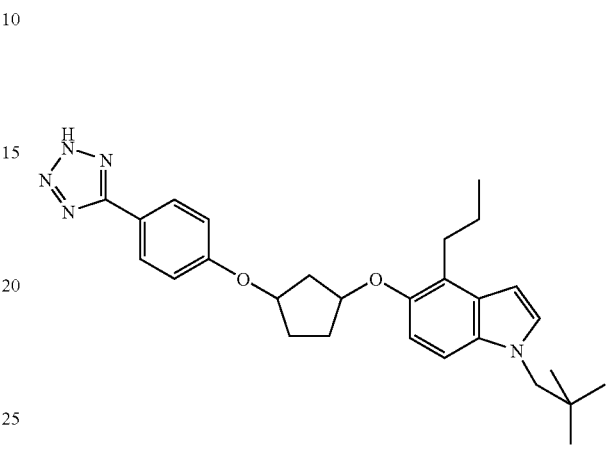

1-(2,2-Dimethyl-propyl)-4-propyl-5-{3-[4-(2H-tetrazol-5-yl)-phenoxy]-cyclopentyloxy}-1H-indole Diethyl azodicarboxylate (7.7 mL, 49 mmol) was added dropwise over 12 min to a solution of 4-hydroxybenzonitrile (3.8 g, 32 mmol), cyclopentane-1,3-diol (5.0 g, 49 mmol), PPh$_3$ (13 g, 49 mmol), and THF (200 mL) at 0° C. under N$_2$. The reaction was allowed to warm to room temperature, maintained for 70 min, reduced to a volume of 50 mL, filtered, concentrated, and purified by silica gel chromatography (hexanes:ethyl acetate—4:1→1:2) to give a white solid. MS (ESI): 204 (M+H). Triethylamine (0.42 mL, 3.1 mmol) was added dropwise over 1 min to a solution of methanesulfonyl chloride (0.09 mL, 1.2 mmol), 4-[(3-hydroxycyclopentyl)oxy]-benzonitrile (0.25 g, 1.2 mmol), and CH$_2$Cl$_2$ (10 mL) at 0° C. under N$_2$. The resulting solution was allowed to warm to rt and maintained for 1.5 hr. Water (2 ml) was added and the mixture stirred for 15 min. The organic layer was extracted with NaHCO$_3$ (5 ml×2), H$_2$O (5 mL×2), and brine (5 mL). The resulting solution was dried (MgSO$_4$), filtered, and concentrated to yield a tan oil. MS (ESI): 282 (M+H). A mixture of the above mesylate (0.12 g, 0.41 mmol), 1-(2,2-dimethylpropyl)-4-propyl-1H-indol-5-ol (0.10 g, 0.41 mmol), K$_2$CO$_3$ (0.17 g, 1.2 mmol), and acetone (4 μL) was heated at 90° C. for 48 h in a closed vessel. The mixture was allowed to cool to rt, filtered, concentrated, and purified by silica gel (hexanes: ethyl acetate—99:1→4:1) to give a white solid. MS (ESI): 431 (M+H). The tetrazole-forming reaction was conducted as outlined in example 1. $^1$H NMR (500 MHz, DMSO) δ 7.96 (d, 2H), 7.26 (d, 1H), 7.21 (d, 1H), 7.14 (d, 2H), 6.87 (d, 1H), 6.38 (d, 1H), 5.11 (m, 1H), 4.93 (m, 1H), 3.90 (s, 2H), 2.77 (t, 2H), 2.27 (m, 2H), 2.13 (m, 2H), 1.88 (m, 2H), 1.61 (m, 2H), 0.94 (t, 3H), 0.93 (s, 9H). MS (ESI): 474 (M+H).

EXAMPLE 58

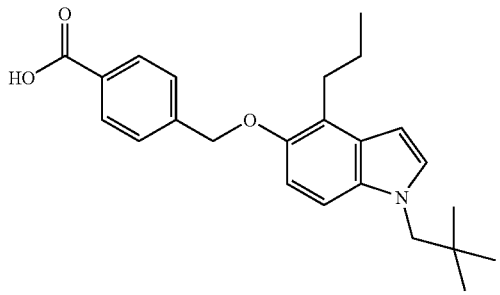

4-[1-(2,2-Dimethyl-propyl)-4-propyl-1H-indol-5-yloxymethyl]-benzoic acid

Triethylamine (1.9 mL, 13 mmol) was added dropwise over 1 min to a solution of methanesulfonyl chloride (0.51 mL, 6.6 mmol), methyl 4-(hydroxymethyl)-benzoate (1.0 g, 6.0 mmol), and CH$_2$Cl$_2$ (40 mL) at 0° C. The resulting solution was allowed to warm to rt and maintained for 1 hr. Water (2 ml) was added and the mixture stirred for 15 min. The organic layer was extracted with NaHCO$_3$ (10 ml×2), H$_2$O (10 mL×2), and brine (10 mL). The resulting solution was dried (MgSO$_4$), filtered, and concentrated to yield a white solid. MS (ESI): 245 (M+H). The above mesylate (0.95 g, 3.9 mmol) was added to a mixture of 1-(2,2-dimethylpropyl)-4-propyl-1H-indol-5-ol (0.73 g, 3.0 mmol), NaH (0.07 g, 3.3 mmol), and DMF (12 mL) at rt, and the reaction was then heated at 100° C. for 2 h. The resulting mixture was allowed to cool to rt, quenched with NaHCO$_3$ (5 mL), poured into H$_2$O (75 mL), and extracted with CH$_2$Cl$_2$ (60 mL×3). The organic extract was washed with H$_2$O (60 mL×5), and then brine (60 mL), dried (MgSO$_4$), filtered and concentrated to yield a tan oil. MS (ESI): 394 (M+H). A similar procedure as outlined in example 26 was followed for the saponification of the above ester. $^1$H NMR (500 MHz, DMSO) δ 12.92 (s, 1H), 7.98 (d, 2H), 7.58 (d, 2H), 7.26 (d, 1H), 7.22 (d, 1H), 6.93 (d, 1H), 6.39 (d, 1H), 5.16 (s, 2H), 3.91 (s, 2H), 2.83 (t, 2H), 1.62 (m, 2H), 0.92 (m, 12H). MS (ESI): 380 (M+H).

EXAMPLE 59

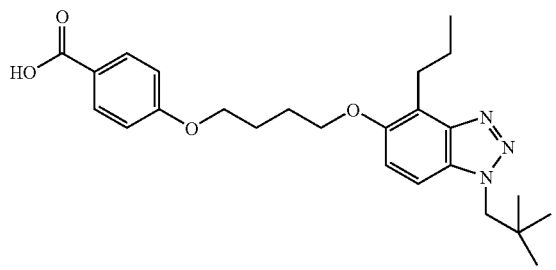

4-{4-[1-(2,2-Dimethyl-propyl)-4-propyl-2H-benzotriazol-5-yloxy]-butoxy}-benzoic acid Similar procedures as outlined in examples 1 & 26 were followed using methyl 4-(4-bromobutoxy)benzoate and the mixture of N-alkylated benzotriazoles from example 6. $^1$H NMR (500 MHz, DMSO) δ 12.58 (bs, 1H), 7.89 (d, 2H), 7.66 (d, 1H), 7.37 (d, 1H), 7.25 (d, 1H), 7.01 (d, 2H), 4.44 (s, 2H), 4.14 (m, 4H), 3.01 (t, 2H), 1.93 (m, 4H), 1.71 (m, 2H), 0.96 (s, 9H), 0.91 (t, 3H). MS (ESI): 440 (M+H).

EXAMPLE 60

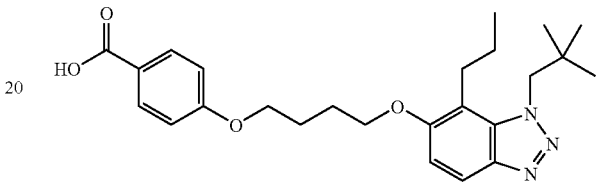

4-{4-[3-(2,2-Dimethyl-propyl)-4-propyl-3H-benzotriazol-5-yloxy]-butoxy}-benzoic acid Isolated from the reaction sequence of example 59. $^1$H NMR (500 MHz, DMSO) δ 12.63 (s, 1H), 7.89 (m, 3H), 7.25 (d, 1H), 7.02 (d, 2H), 7.01 (d, 2H), 4.50 (s, 2H), 4.15 (m, 4H), 2.90 (t, 2H), 1.93 (m, 4H), 1.67 (m, 2H), 0.97 (s, 9H), 0.91 (t, 3H). MS (ESI): 440 (M+H).

EXAMPLE 61

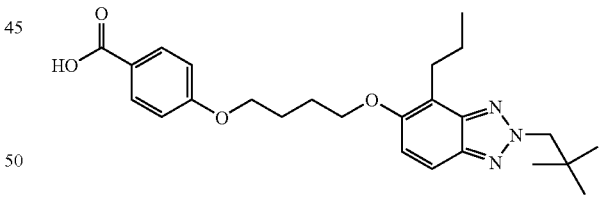

4-{4-[2-(2,2-Dimethyl-propyl)-4-propyl-1H-benzotriazol-5-yloxy]-butoxy}-benzoic acid Isolated from the reaction sequence of example 59. $^1$H NMR (500 MHz, DMSO) δ 12.63 (s, 1H), 7.86 (d, 2H), 7.74 (d, 1H), 7.33 (d, 1H), 7.01 (d, 2H), 4.50 (s, 2H), 4.15 (m, 4H), 2.90 (t, 2H), 1.93 (m, 4H), 1.67 (m, 2H), 0.97 (s, 9H), 0.91 (t, 3H). MS (ESI): 440 (M+H).

EXAMPLE 62

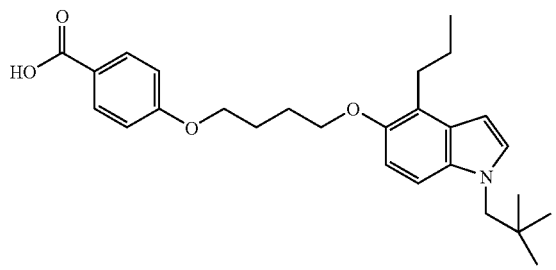

4-{4-[1-(2,2-Dimethyl-propyl)-4-propyl-1H-indol-5-yloxy]-butoxy}-benzoic acid

Similar procedures as outlined in examples 1 & 26 were followed using methyl 4-(4-bromobutoxy)benzoate and 1-(2,2-dimethylpropyl)-4-propyl-1H-indol-5-ol. $^1$H NMR (500 MHz, DMSO) δ 12.64 (s, 1H), 7.92 (d, 2H), 7.24 (d, 1H), 7.20 (s, 1H), 7.02 (d, 2H), 6.87 (d, 1H), 6.37 (d, 1H), 4.14 (t, 2H), 4.01 (t, 2H), 3.90 (s, 2H), 2.77 (t, 2H), 1.95 (m, 2H), 1.88 (m, 2H), 1.59 (m, 2H), 0.92 (s, 9H), 0.90 (t, 3H). MS (ESI): 438 (M+H).

EXAMPLE 63

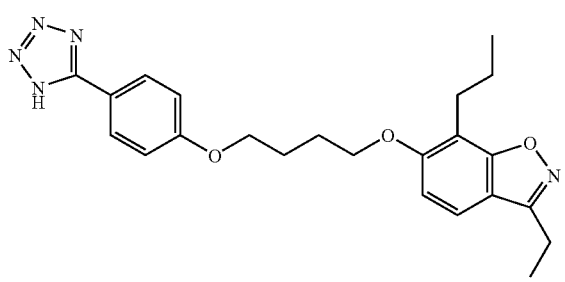

3-ethyl-7-propyl-6-{4-[4-(1H-tetrazol-5-yl)phenoxy]butoxy}-1,2-benzisoxazole

Similar procedures as outlined in example 1 were followed using 3-ethyl-7-propyl-1,2-benzisoxazol-6-ol. $^1$H NMR (CD$_3$OD, 500 MHz) δ 8.10 (m, 2H), 7.70 (m, 1H), 7.20 (m, 1H), 7.10 (m, 2H), 4.20 (m, 4H), 3.10 (m, 4H), 2.10 (m, 4H), 1.80 (m, 2H), 1.50 (m, 3H), 1.05 (m, 3H). MS (ESI: 422 (M+H).

EXAMPLE 64

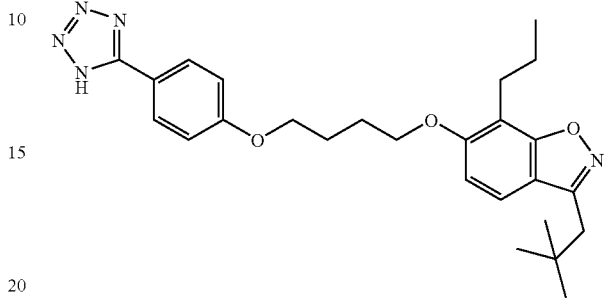

3-(2,2-dimethylpropyl)-7-propyl-6-{4-[4-(1H-tetrazol-5-yl)phenoxy]butoxy}-1,2-benzisoxazole Similar procedures as outlined in example 1 were followed using 3-(2,2-dimethylpropyl)-7-propyl-1,2-benzisoxazol-6-ol. $^1$H NMR (CD$_3$OD, 500 MHz) δ 8.00 (d, 2H), 7.60 (d, 1H), 7.15 (d, 1H), 7.05 (d, 2H), 4.20 (d, 4H), 3.35 (m, 4H), 2.10 (m, 4H), 1.70 (m, 2H), 1.10 (s, 9H), 1.00 (m, 3H). MS (ESI): 464 (M+H).

EXAMPLE 65

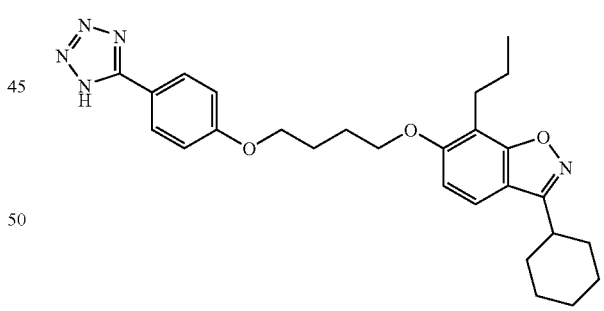

3-cyclohexyl-7-propyl-6-{4-[4-(1H-tetrazol-5-yl)phenoxy]butoxy}-1,2-benzisoxazole Similar procedures as outlined in example 1 were followed using 3-cyclo-hexyl-7-propyl-1,2-benzisoxazol-6-ol. $^1$H NMR (CD$_3$OD, 500 MHz) δ 8.00 (d, 2H), 7.45 (d, 1H), 7.05

(m, 3H), 4.20 (m, 4H), 3.30 (m, 4H), 3.00 (m, 3H), 2.10 (m, 4H), 1.80 (m, 6H), 1.50 (m, 2H), 1.00 (m, 3H). MS (ESI): 476 (M+H).

EXAMPLE 66

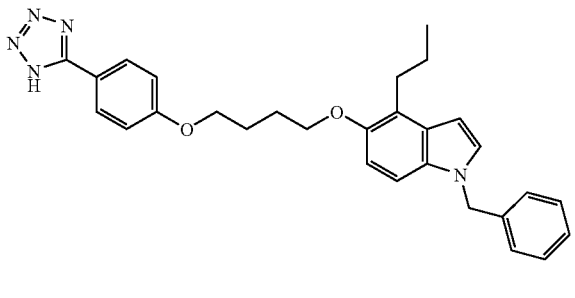

1-benzyl-4-propyl-5-{4-[4-(1H-tetrazol-5-yl)phenoxy]butoxy}-1H-indole

A similar procedure as outlined in example 42 was followed using (bromomethyl)benzene. $^1$H NMR (500 MHz, DMSO) δ 7.97 (d, 2H), 7.43 (d, 1H), 7.37-7.07 (m, 8H), 6.87 (d, 1H), 6.42 (d, 1H), 5.35 (s, 2H), 4.15 (t, 2H), 4.01 (t, 2H), 2.78 (t, 2H), 1.97-1.87 (m, 4H), 1.62-1.56 (m, 2H), 0.90 (t, 3H). MS (ESI): 482 (M+H).

EXAMPLE 67

1-(2,2-dimethylpropanoyl)-4-propyl-5-{4-[4-(1H-tetrazol-5-yl)phenoxy]butoxy}-1H-indole A similar procedure as outlined in example 42 was followed using 2,2-dimethylpropanoyl chloride. $^1$H NMR (500 MHz, DMSO) δ 8.17 (d, 1H), 8.04 (d, 1H), 7.97 (d, 2H), 7.17 (d, 2H), 7.02 (d, 1H), 6.73 (d, 1H), 4.16 (t, 2H), 4.07 (t, 2H), 2.78 (t, 2H), 1.96-1.92 (m, 4H), 1.60-1.53 (m, 2H), 1.44 (s, 9H) 0.87 (t, 3H). MS (ESI): 476.3 (M+H).

EXAMPLE 68

1-(4-methylbenzyl-4-propyl-5-{4-[4-(1H-tetrazol-5-yl)phenoxy]butoxy}-1H-indole

A similar procedure as outlined in example 42 was followed using 1-(bromomethyl)-4-methylbenzene. $^1$H NMR (500 MHz, DMSO) δ 7.97 (d, 2H), 7.41 (d, 1H), 7.18-7.10 (m, 7H), 6.86 (d, 1H), 6.40 (d, 1H), 5.28 (s, 2H), 4.15 (t, 2H), 4.00 (t, 2H), 2.77 (t, 2H), 2.24 (s, 3H), 1.97-1.87 (m, 4H), 1.60-1.54 (m, 2H) 0.87 (t, 3H). MS (ESI): 496 (M+H).

EXAMPLE 69

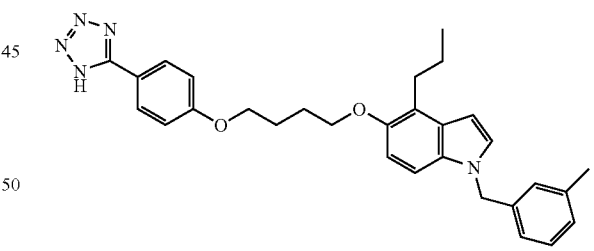

1-(3-methylbenzyl-4-propyl-5-{4-[4-(1H-tetrazol-5-yl)phenoxy]butoxy}-1H-indole

A similar procedure as outlined in example 42 was followed using 1-(bromomethyl)-3-methylbenzene. $^1$H NMR (500 MHz, DMSO) δ 7.97 (d, 2H), 7.42 (d, 1H), 7.20-7.14 (m, 4H), 7.06-7.05 (m, 2H), 6.98-6.97 (m, 1H), 6.87 (d, 1H), 6.41

(d, 1H), 5.30 (s, 2H), 4.15 (t, 2H), 4.00 (t, 2H), 2.78 (t, 2H), 2.24 (s, 3H), 1.97-1.87 (m, 4H), 1.60-1.56 (m, 2H), 0.89 (t, 3H). MS (ESI): 496 (M+H).

EXAMPLE 70

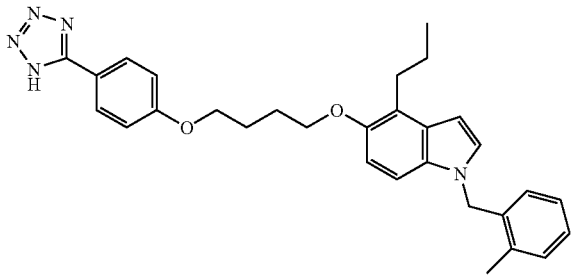

1-(2-methylbenzyl-4-propyl-5-{4-[4-(1H-tetrazol-5-yl)phenoxy]butoxy}-1H-indole

A similar procedure as outlined in example 42 was followed using 1-(bromomethyl)-2-methylbenzene. $^1$H NMR (500 MHz, DMSO) δ 7.97 (d, 2H), 7.27 (d, 1H), 7.21-7.04 (m, 6H), 6.87 (d, 1H), 6.55 (d, 1H), 6.45 (d, 1H), 5.35 (s, 2H), 4.16 (t, 2H), 4.01 (t, 2H), 2.79 (t, 2H), 2.30 (s, 3H), 1.96-1.90 (m, 4H), 1.63-1.59 (m, 2H), 0.86 (t, 3H). MS (ESI): 496 (M+H).

EXAMPLE 71

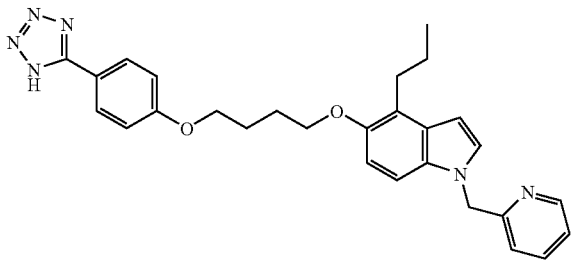

4-propyl-1-(pyridin-2-ylmethyl)-5-{4-[4-(1H-tetrazol-5-yl)phenoxy]butoxy}-1H-indole A similar procedure as outlined in example 42 was followed using 2-(bromomethyl)pyridinium bromide. $^1$H NMR (500 MHz, DMSO) δ 8.55 (d, 1H), 7.97 (d, 2H), 7.76-7.71 (m, 1H), 7.40 (d, 1H), 7.31-7.24 (m, 1H), 7.18-7.12 (m, 3H), 7.99 (d, 1H), 6.87 (d, 1H), 6.45 (d, 1H), 4.16 (t, 2H), 4.00 (t, 2H), 2.79 (t, 2H), 1.97-1.87 (m, 4H), 1.33-1.24 (m, 2H), 0.89 (t, 3H). MS (ESI): 483 (M+H).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above.

What is claimed is:
1. A compound of the formula I:

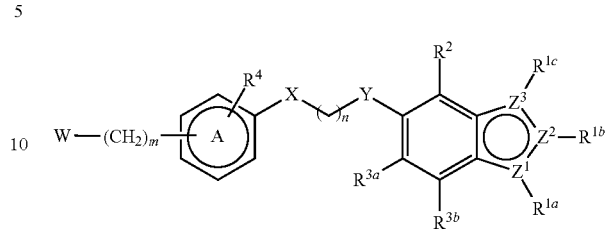

wherein:
A is phenyl;
W is selected from the group consisting of:
(1) -tetrazolyl, and
(2) —CO$_2$H;
X is selected from the group consisting of:
(1) —O—,
(2) —O—C$_{1-6}$alkanediyl-,
(3) —O—C$_{1-6}$alkenediyl-,
(4) —O—C$_{3-7}$cycloalkanediyl-, and
(5) —O-phenylene-, wherein the phenylene is unsubstituted or substituted with C$_{1-6}$alkyl, or halogen;
Y is
—O—;
Z$^1$, Z$^2$ and Z$^3$ are N such that together with the fused phenyl ring they form a benzotriazolyl ring;
R$^{1a}$, R$^{1b}$ and R$^{1c}$ may be absent if the valency at Z$^1$, Z$^2$ or Z$^3$ does not permit such substitution and are independently selected from the group consisting of:
(1) hydrogen,
(2) C$_{1-6}$alkyl, which is unsubstituted or substituted with a substituent selected from:
(a) halogen,
(b) hydroxyl,
(c) phenyl, wherein the phenyl is unsubstituted or substituted with 1-5substituents independently selected from halogen, cyano, CF$_3$, hydroxyl, C$_{1-6}$alkyl, and OC$_{1-6}$alkyl,
(d) C$_{3-7}$cycloalkyl, which is unsubstituted or substituted with halogen, hydroxyl or phenyl,
(e) naphthyl, which is unsubstituted or substituted with halogen, C$_{1-6}$alkyl or phenyl,
(f) —CO—C$_{1-6}$alkyl, and
(g) —COO—C$_{1-6}$alkyl,
(3) C$_{3-7}$cycloalkyl, which is unsubstituted or substituted with halogen, C$_{1-6}$alkyl, hydroxyl or phenyl,
(4) phenyl, wherein the phenyl is unsubstituted or substituted with 1-5 substituents independently selected from halogen, hydroxyl, cyano, CF$_3$, C$_{1-6}$alkyl, and OC$_{1-6}$alkyl, wherein the C$_{1-6}$alkyl and OC$_{1-6}$alkyl are linear or branched and optionally substituted with 1-5 halogen,
(5) —CO—C$_{1-6}$alkyl, and
(6) —COO—C$_{1-6}$alkyl;
R$^2$ is selected from the group consisting of:
(1) hydrogen,
(2) halogen,
(3) hydroxyl,
(4) OC$_{1-6}$alkyl,
(5) C$_{2-6}$alkenyl, and
(6) C$_{1-6}$alkyl, which is unsubstituted or substituted with halogen, hydroxyl or phenyl;

$R^{3a}$ and $R^{3b}$ are selected from the group consisting of:
(1) hydrogen,
(2) halogen,
(3) $C_{1-6}$alkyl, which is unsubstituted or substituted with halogen, hydroxyl or phenyl, and
(4) $OC_{1-6}$alkyl;

$R^4$ may include multiple substituents and is independently selected from the group consisting of:
(1) hydrogen,
(2) halogen,
(3) $C_{1-6}$alkyl, and
(4) —O—$C_{1-6}$alkyl;

m is an integer selected from 0, 1, 2 and 3;
n is an integer selected from 0, 1, 2, 3, 4, 5 and 6;
or a pharmaceutically acceptable salt thereof.

2. The compound of claim 1 which is selected from the group consisting of:

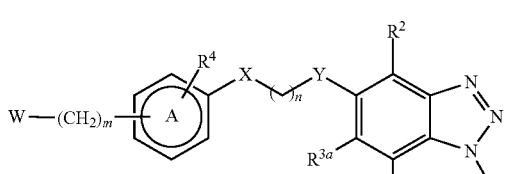

If

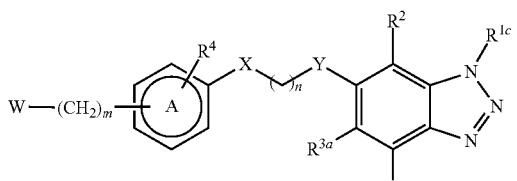

Ig

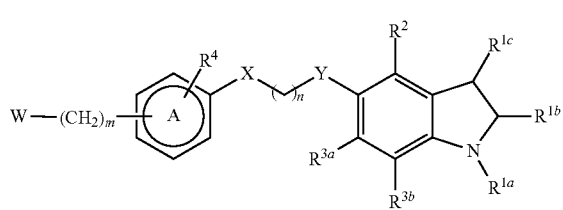

Ic

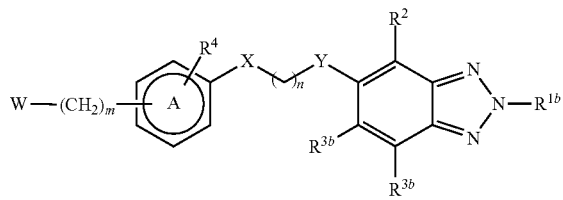

Ih or a pharmaceutically acceptable salt thereof.

3. The compound of claim 2 which is:

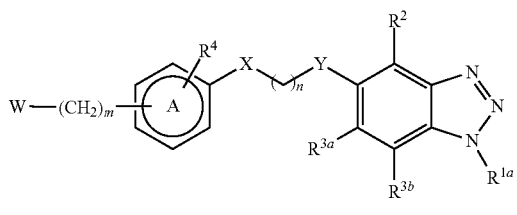

If

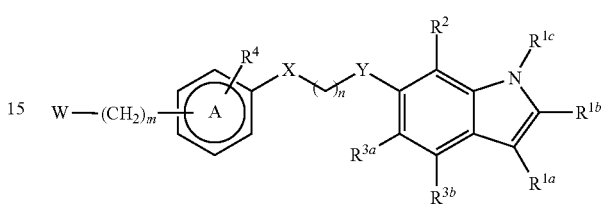

Ib or a pharmaceutically acceptable salt thereof.

4. The compound of claim 1 wherein $R^{1a}$, $R^{1b}$ and $R^{1c}$ are independently selected from hydrogen and $C_{1-6}$alkyl, which is unsubstituted or substituted with:
$C_{3-7}$cycloalkyl.

5. The compound of claim 1 wherein $R^{1a}$, $R^{1b}$ and $R^{1c}$ are independently selected from hydrogen, $CH_3$, $CH_2CH_2CH_3$, $CH_2CH(CH_3)_2$, $CH_2CH_2CH_2CH_3$, $CH_2C(CH_3)_3$, $CH_2$-cyclopropyl, $CH_2$-cyclohexyl and phenyl.

6. The compound of claim 5 wherein $R^{1a}$, $R^{1b}$ and $R^{1c}$ are independently selected from hydrogen, $CH_2CH(CH_3)_2$, $CH_2CH_2CH_2CH_3$, $CH_2C(CH_3)_3$ and $CH_2$-cyclohexyl.

7. The compound of claim 6 wherein $R^{1a}$ is $CH_2C(CH_3)_3$.

8. The compound of claim 6 wherein $R^{1a}$ is $CH_2$-cyclohexyl.

9. The compound of claim 1 wherein $R^2$ is selected from the group consisting of: hydrogen, methyl, propyl, allyl and bromo.

10. The compound of claim 1 wherein $R^3a$ and $R^3b$ are hydrogen and $R^4$ is hydrogen.

11. The compound of claim 1 wherein m is 0 or 1.

12. The compound of claim 1 wherein n is 1.

13. The compound of claim 1 wherein n is 4.

14. A compound which is selected from the group consisting of:
1-(2,2-dimethylpropyl)-4-propyl-5-{4-[4-(1H-tetrazol-5-yl)phenoxy]butoxy}-1H-1,2,3-benzotriazole;
1-(2,2-dimethylpropyl)-7-propyl-6-{4-[4-(1H-tetrazol-5-yl)phenoxy]butoxy}-1H-1,2,3-benzotriazole;
1-(2,2-dimethylpropyl)-5-{4-[4-(1H-tetrazol-5-yl)phenoxy]butoxy}-1H-1,2,3-benzotriazole;
1-(2,2-dimethylpropyl)-6-{4-[4-(1H-tetrazol-5-yl)phenoxy]butoxy}-1H-1,2,3-benzotriazole;
4-bromo-1-(2,2-dimethylpropyl)-5-{4-[4-(1H-tetrazol-5-yl)phenoxy]butoxy}-1H-1,2,3-benzotriazole;
7-bromo-1-(2,2-dimethylpropyl)-6-{4-[4-(1H-tetrazol-5-yl)phenoxy]butoxy}-1H-1,2,3-benzotriazole;
4-{4-[1-(2,2-Dimethyl-propyl)-4-propyl-2H-benzotriazol-5-yloxy]-butoxy}-benzoic acid;
4-{4-[3-(2,2-Dimethyl-propyl)-4-propyl-3H-benzotriazol-5-yloxy]-butoxy}-benzoic acid;
4-{4-[2-(2,2-Dimethyl-propyl)-4-propyl-1H-benzotriazol-5-yloxy]-butoxy}-benzoic acid;
or a pharmaceutically acceptable salt thereof.

15. A pharmaceutical composition which comprises an inert carrier and the compound of claim 1 or a pharmaceutically acceptable salt thereof.

* * * * *